United States Patent [19]
Jeffcoat et al.

[11] Patent Number: 5,871,756
[45] Date of Patent: Feb. 16, 1999

[54] COSMETICS CONTAINING THERMALLY-INHIBITED STARCHES

[75] Inventors: Roger Jeffcoat, Bridgewater; Joseph Pasapane, Morristown; Donna L. Ronco, Oxford; Daniel B. Solarek, Belle Mead; Douglas J. Hanchett, Wharton, all of N.J.

[73] Assignee: National Starch and Chemical Investment Holding Corporation, Wilmington, Del.

[21] Appl. No.: 594,198

[22] Filed: Jan. 31, 1996

Related U.S. Application Data

[63] Continuation-in-part of PCT/US96/00613, Jan. 17, 1996 which is a continuation-in-part of Ser. No. 375,320, Jan. 18, 1995, abandoned.

[51] Int. Cl.⁶ .......................................................... A61K 7/48
[52] U.S. Cl. ............................. 424/401; 424/47; 424/59; 424/61; 424/64; 424/65; 424/69; 424/70.1; 424/70.2; 424/70.6; 424/70.7; 424/73; 424/DIG. 1; 424/DIG. 2; 424/DIG. 3; 424/DIG. 5; 514/60
[58] Field of Search .................................. 424/401, 70.1, 424/47, 59, 61, 65, 64, 69, 70.2, 70.6, 70.7, 73, DIG. 1, DIG. 2, DIG. 3, DIG. 5; 514/60

[56] References Cited

U.S. PATENT DOCUMENTS

| | | | |
|---|---|---|---|
| 2,274,789 | 3/1942 | Horesi | 127/38 |
| 2,317,752 | 4/1943 | Fuller | 127/33 |
| 2,373,016 | 4/1945 | Daly et al. | 127/70 |
| 2,427,328 | 9/1947 | Schopmeyer et al. | 127/32 |
| 2,590,912 | 4/1952 | Yarber | 127/32 |
| 2,661,349 | 2/1953 | Caldwell et al. | 260/224 |
| 2,791,512 | 5/1957 | Hatch et al. | 106/208 |
| 2,897,086 | 7/1959 | Sowell et al. | 99/139 |
| 2,951,776 | 9/1960 | Scallet et al. | 127/71 |
| 3,155,527 | 11/1964 | Mentzer | 106/210 |
| 3,331,697 | 7/1967 | Salamon | 106/213 |
| 3,399,081 | 8/1968 | Bernetti et al. | 127/71 |
| 3,408,214 | 10/1968 | Mentzer | 106/212 |
| 3,463,668 | 8/1969 | Evans et al. | 127/32 |
| 3,477,903 | 11/1969 | Semegran et al. | 161/266 |
| 3,490,917 | 1/1970 | Doe et al. | 99/93 |
| 3,515,591 | 6/1970 | Feldman et al. | 127/32 |
| 3,563,798 | 2/1971 | Germino et al. | 127/32 |
| 3,578,497 | 5/1971 | Hjermstad | 127/32 |
| 3,607,394 | 9/1971 | Germino et al. | 127/32 |
| 3,607,396 | 9/1971 | Germino et al. | 127/71 |
| 3,640,756 | 2/1972 | Beersma et al. | 117/76 |
| 3,690,938 | 9/1972 | Swift | 117/122 |
| 3,725,387 | 4/1973 | McClendon et al. | 260/233.3 |
| 3,810,783 | 5/1974 | Bomball | 117/122 |
| 3,844,807 | 10/1974 | Bramel | 106/213 |
| 3,949,104 | 4/1976 | Cheng et al. | 426/578 |
| 3,950,593 | 4/1976 | Bomball | 428/476 |
| 3,967,975 | 7/1976 | Idaszak | 127/23 |
| 3,977,897 | 8/1976 | Wurzburg et al. | 127/71 |
| 4,013,799 | 3/1977 | Smalligan et al. | 426/578 |
| 4,131,574 | 12/1978 | Isherwood et al. | 260/17.3 |
| 4,256,509 | 3/1981 | Tuschhoff et al. | 127/32 |
| 4,266,348 | 5/1981 | Ledding | 34/10 |
| 4,280,851 | 7/1981 | Pitchon et al. | 127/33 |
| 4,303,451 | 12/1981 | Seidel et al. | 127/32 |
| 4,303,452 | 12/1981 | Ohira et al. | 127/32 |
| 4,366,275 | 12/1982 | Silano et al. | 524/47 |
| 4,391,836 | 7/1983 | Chiu | 426/578 |
| 4,428,972 | 1/1984 | Wurzburg et al. | 426/578 |
| 4,465,702 | 8/1984 | Eastman et al. | 426/578 |
| 4,491,483 | 1/1985 | Dudacek et al. | 127/33 |
| 4,575,395 | 3/1986 | Rudin | 127/32 |
| 4,600,472 | 7/1986 | Pitchon et al. | 159/4.4 |
| 4,610,760 | 9/1986 | Kirkpatrick et al. | 159/4.01 |
| 4,847,371 | 7/1989 | Schara et al. | 536/111 |
| 5,037,929 | 8/1991 | Rajagopalan et al. | 426/578 |

(List continued on next page.)

FOREIGN PATENT DOCUMENTS

| | | |
|---|---|---|
| 1 150 934 | 8/1983 | Canada . |
| 0 129 227 A1 | 12/1984 | European Pat. Off. . |
| 0 257 338 A2 | 3/1988 | European Pat. Off. . |
| 0 321 216 A2 | 6/1989 | European Pat. Off. . |
| 0 415 385 A2 | 3/1991 | European Pat. Off. . |
| 0 490 424 A1 | 6/1992 | European Pat. Off. . |
| 61-254602 | 11/1986 | Japan . |
| 63/194725 | 5/1987 | Japan . |
| 263897 | 12/1926 | United Kingdom . |
| 530226 | 12/1940 | United Kingdom . |
| 595552 | 12/1947 | United Kingdom . |
| 1224281 | 10/1971 | United Kingdom . |
| 95/04082 | 2/1995 | WIPO . |

OTHER PUBLICATIONS

J.W. Donovan et al., *Cereal Chemistry*, "Differential Scanning Calorimetry of Heat–Moisture Treated Wheat and Potato Starches", vol. 60, No. 5, pp 381–387 (1983).

Cristina Ferrero et al., *Journal of Food Processing and Preservation*, "Stability of Frozen Starch Pastes: Effect of Freezing, Storage and Xanthan Gum Addition", vol. 17, pp. 191–211 (1993).

Dong–Hyun Lee et al., *Chem. Eng. Technol.*, "Drying Characteristics of Starch in an Inert Medium Fluidized Bed", vol. 16, pp. 263–269 (1993).

Irving Martin, *Journal of Applied Polymer Science*, "Crosslinking of Starch by Alkaline Roasting", vol. 11, No. 5, pp. 1283–1288 (May 1967).

Rolf Stute, *Starch/Stärke*, "Hydrothermal Modification of Starches: The Difference between Annealing and Heat/Moisture–Treatment", vol. 44, No. 6, pp. 205–214 (1992).

*Primary Examiner*—Jyothsna Venkat
*Attorney, Agent, or Firm*—Margaret B. Kelley

[57] ABSTRACT

Thermally-inhibited starches and flours are used in cosmetic compositions such as skin and hair care products as emulsifiers, thickeners, and aesthetic control agents. The starch or flour is inhibited by dehydrating the starch or flour to anhydrous or substantially anhydrous and then heat treating the dehydrated starch or flour for a time and at a temperature sufficient to inhibit the starch or flour and improve its viscosity stability when dispersed in water. The dehydration may be a thermal or a non-thermal dehydration (e.g., by alcohol extraction or freeze-drying). Preferably, the pH of the starch or flour is adjusted to a neutral or above (e.g., pH 8–9.5) prior to the dehydration and heat treatment.

19 Claims, No Drawings

U.S. PATENT DOCUMENTS

| | | | |
|---|---|---|---|
| 5,085,228 | 2/1992 | Mooney et al. | 131/37 |
| 5,087,649 | 2/1992 | Wegner et al. | 524/30 |
| 5,149,799 | 9/1992 | Rubens | 536/102 |
| 5,155,140 | 10/1992 | Marten et al. | 523/100 |
| 5,181,959 | 1/1993 | Nagai et al. | 106/211 |
| 5,329,004 | 7/1994 | Eden et al. | 536/109 |
| 5,368,690 | 11/1994 | Solarek et al. | 162/175 |

COSMETICS CONTAINING THERMALLY-INHIBITED STARCHES

This application is a continuation-in-part of pending PCT application (PCT/US96/00613) filed Jan. 17, 1996 which is a CIP of U.S. application Ser. No. 08/375,320 filed Jan. 18, 1995 now abandoned.

BACKGROUND ART OF THE INVENTION

This invention relates to cosmetic skin and hair care compositions containing starches and flours as thickeners, emulsion stabilizers, and aesthetic modifiers.

Heat Treatment of Starches and Flours

Heat/moisture treatment and annealing of starches and/or flours are taught in the literature and distinguished by the amount of water present. "Annealing" involves slurrying a granular starch with excess water at temperatures below the starch's or flour's gelatinization temperature. "Heat/moisture-treatment" involves a semi-dry treatment at temperatures below the starch's or flour's gelatinization temperature, with no added moisture and with the only moisture present being that normally present in a starch granule (which is typically 10% or more).

In the following discussion, a history of the various heat/moisture and annealing treatments of starch and/or flour is set out.

GB 263,897 (accepted Dec. 24, 1926) discloses an improvement in the heat treatment process of GB 228,829. The process of the '829 patent involves dry heating flour or wheat to a point at which substantially all of the gluten is rendered non-retainable in a washing test and then blending the treated flour or wheat with untreated flour or wheat to provide a blend having superior strength. The improvement of the '897 patent is continuing the dry heating, without, however, gelatinizing the starch, for a considerable time beyond that necessary to render all of the gluten non-retainable. "Dry-heating" excludes heating in a steam atmosphere or an atmosphere containing considerable quantities of water vapor which would tend to gelatinize the starch. The wheat or flour may contain the usual amount of moisture, preferably not greater than 15%. The heat treatment may exceed 7 hours at 77°–93° C. (170°–200° F.), e.g., 8 to 14 hours at 82° C. (180° F.) or 6 hours at 100° C. (212° F.).

GB 530,226 (accepted Dec. 6, 1940) discloses a method for drying a starch cake containing about 40–50% water with hot air or another gas at 149° C. (300° F.) or above without gelatinizing the starch. The starch cake is disintegrated by milling it to a finely divided state prior to drying.

GB-595,552 (accepted Dec. 9, 1947) discloses treatment of starch, more particularly a corn starch, which involves drying the starch to a relatively low moisture content of 1–2%, not exceeding 3%, and subsequently dry heating the substantially moisture-free starch at 115°–126° C. for 1 to 3 hours. The treatment is intended to render the starch free from thermophilic bacteria. The starch should not be heated longer than necessary to effect the desired sterilization.

U.S. Pat. No. 3,490,917 (issued Jan. 20, 1970 to C. A. F. Doe et al.) discloses a process for preparing a non-chlorinated cake flour suitable for use in cakes and sponges having a high sugar to flour ratio. The starch or a flour in which the gluten is substantially or completely detached from the starch granules is heated to a temperature of from 100°–140° C. and then cooled. The conditions are selected so that dextrinization does not occur, e.g., about 15 minutes at 100°–115° C. and no hold and rapid cooling at the higher temperatures. The heat treatment should be carried out under conditions which allow the water vapor to escape. The reduction in moisture content due to the heat treatment depends upon the temperature employed. At treatment temperatures of 100°–105° C., the moisture content is reduced from 10–12% to 8–9%, by weight, while at medium and high temperatures the moisture content is typically reduced to 7% or less. Preferably, during cooling the moisture is allowed to reach moisture equilibrium with the atmosphere. The gelatinization temperature of the heat treated starch or flour is approximately 0.5°–1° C. higher than that of a comparable chlorinated flour or starch. The heating can be carried out in many ways, including heating in a hot air fluidized bed.

U.S. Pat. No. 3,578,497 (issued May 11, 1971 to E. T. Hjermstad) discloses a process for non-chemically improving the paste and gel properties of potato starch and imparting a swelling temperature as much as 20° to 30° F. higher. A concentrated suspension (20–40% dry solids) at a neutral pH (5.5–8.0, preferably 6–7.5) is heated either for a long time at a relatively low temperature or for a short time at successively higher temperatures. The suspension is first heated at a temperature below the incipient swelling temperature of the particular batch of starch being treated (preferably 49° C.–120° F.). Then the temperature is gradually raised until a temperature well above the original swelling temperature is attained. It is essential that swelling be avoided during the different heating periods so that gelatinization does not occur. After this steeping treatment the starch has a higher degree of granular stability. It resists rapid gelatinization and produces a rising or fairly flat viscosity curve on cooling. The pastes are very short textured, non-gumming, non-slimy, cloudy and non-cohesive. They form firm gels on cooling and aging.

U.S. Pat. No. 3,977,897 (issued Aug. 31, 1976 to Wurzburg et al.) discloses a method for preparing non-chemically inhibited amylose-containing starches. Both cereal and root starches can be inhibited, but the inhibition effects are more observable with root starches. Amylose-free starches, such as waxy corn starch, show no or very slight inhibition. The Brabender viscosity of cooked pastes derived from the treated starch was used to determine the inhibition level. Inhibition was indicated by a delayed peak time in the case of the treated corn starch, by the lack of a peak and a higher final viscosity in the case of the treated achira starch, and by the loss of cohesiveness in the case of the treated tapioca starch. The granular starch is suspended in water in the presence of salts which raise the starch's gelatinization temperature so that the suspension may be heated to high temperatures without causing the starch granules to swell and rupture yielding a gelatinized product. The preferred salts are sodium, ammonium, magnesium or potassium sulfate; sodium, potassium or ammonium chloride; and sodium, potassium or ammonium phosphate. About 10–60 parts of salt are used per 100 parts by weight of starch. Preferably, about 110 to 220 parts of water are used per 100 parts by weight of starch. The suspension is heated at 50°–100° C., preferably 60°–90° C., for about 0.5 to 30 hours. The pH of the suspension is maintained at about 3–9, preferably 4–7. Highly alkaline systems, i.e., pH levels above 9 retard inhibition.

U.S. Pat. No. 4,013,799 (issued Mar. 22, 1977, to Smalligan et al.) discloses heating a tapioca starch above its gelatinization temperature with insufficient moisture (15 to 35% by total weight) to produce gelatinization. The starch is heated to 70°–130° C. for 1 to 72 hours. The starch is used as a thickener in wet, pre-cooked baby foods having a pH below about 4.5.

U.S. Pat. No. 4,303,451 (issued Dec. 1, 1981 to Seidel et al.) discloses a method for preparing a pregelatinized waxy maize starch having improved flavor characteristics reminiscent of a tapioca starch. The starch is heat treated at 120°–200° C. for 15 to 20 minutes. The pregelatinized starch has gel strength and viscosity characteristics suitable for use in pudding mixes.

U.S. Pat. No. 4,303,452 (issued Dec. 1, 1981 to Ohira et al.) discloses smoking a waxy maize starch to improve gel strength and impart a smoky taste. In order to counteract the smoke's acidity and to obtain a final product with a pH of 4–7, the pH of the starch is raised to pH 9–11 before smoking. The preferred water content of the starch during smoking is 10–20%

The article "Differential Scanning Calorimetry of Heat-Moisture Treated Wheat and Potato Starches" by J. W. Donovan et al. in *Cereal Chemistry, Vol.* 60, No. 5, pp. 381–387 (1983) discloses that the gelatinization temperature of the starches increased as a result of the heat/moisture treatment or annealing. See also the article "A DSC Study Of The Effect Annealing On Gelatinization Behavior Of Corn Starch" by B. R. Krueger et al. in Journal of Food Science, Vol. 52, No. 3, pp. 715–718 (1987).

U.S. Pat. No. 4,391,836 (issued Jul. 5, 1983 to C. -W. Chiu) discloses instant gelling tapioca and potato starches which are non-granular and which have a reduced viscosity. Unmodified potato and tapioca starches do not normally gel. The starches of the patent are rendered non-granular and cold-water-dispersible by forming an aqueous slurry of the native starch at a pH of about 5–12 and then drum-drying the slurry. The starches are rendered gelling by heat treating the drum-dried starch for about 1.5 to 24 hours at 125°–180° C. to reduce the viscosity to within defined Brabender viscosity limitations.

U.S. Pat. No. 4,491,483 (issued Jan. 1, 1985 to W. E. Dudacek et al.) discloses subjecting a semi-moist blend of a granular starch with at least 0.25 wt. % of a fatty acid surfactant and sufficient water (about 10–40 wt. %) to a heat-moisture treatment at from about 50°–120° C., followed by drying to about 5–15 wt. %, preferably 10 wt. %, moisture. The heat-moisture treated starch-surfactant product is characterized by a hot water dispersibility of from about 60–100% and a higher pasting temperature than the granular starch from which it is derived. Preferably, the treatment takes place in a closed container so that the moisture can be maintained at a constant level. The preferred conditions are 3 to 16 hours at 60°–90° C. Degradation and dextrinization reactions are undesirable as they destroy the thickening ability of the starch. The use of conditions, such as, e.g., 35% moisture at 90° C. for 16 hours results in reduced paste viscosity. It is believed the presence of the surfactant during the treatment permits formation of a complex within the partially swollen starch matrix with straight chain portions of the starch molecules. The limited moisture environment allows complex formation without gelatinization.

Japanese Patent Publication No. 61-254602, (published Dec. 11, 1987) discloses a wet and dry method for heating waxy corn starch and derivatives thereof to impart emulsification properties. The wet or dry starch is heated at 100°–200° C., preferably 130°–150° C., for 0.5 to 6 hours. In the dry method, the water content is 10%, preferably 5%, or less. In the wet method, the water content is 5 to 50%, preferably 20–30%. The pH is 3.5–8, preferably 4–5.

The article "Hydrothermal Modification of Starches: The Difference between Annealing and Heat/Moisture-Treatment", by Rolf Stute, *Starch/Stärke* Vol. 44, No. 6, pp. 205–214 (1992) reports almost identical modifications in the properties of potato starch with annealing and heat/moisture treatments even through the alteration of the granular structure is different. The Brabender curves of the heat/moisture-treated and annealed potato starches show the same typical changes, including a higher gelatinization temperature and a lower peak viscosity or no peak. The DSC curves also show a shift to higher gelatinization temperatures for both treatments. A combined treatment involving annealing a heat/moisture-treated potato starch leads to a further increase in gelatinization temperature without detectable changes in gelatinization enthalapy and with retention of the viscosity changes caused by the heat treatment. A combined treatment involving annealing a heat/moisture-treat potato starch does not lower the gelatinization temperature, when compared to the base starch, and increases the gelatinization temperature at higher heat/moisture treatment levels.

Chemical Crosslinking of Starches and Flours

Starches and flours are chemically modified with difunctional reagents such as phosphorus oxychloride, sodium trimetaphosphate, mixed adipic/acetic anhydride, and epichlorohydrin to produce chemically crosslinked starches having excellent tolerance to processing variables such as heat, shear, and pH extremes. Such chemically crosslinked starches (also referred to as "inhibited starches") provide a desirable smooth texture and possess viscosity stability throughout processing operations and normal shelf life.

In contrast, when unmodified (i.e., non-crosslinked) starches, particularly waxy-based starches, are gelatinized, they reach a peak viscosity which soon begins to breakdown, lose thickening capacity and textural qualities, and behave unpredictably during storage as a result of the stresses encountered during processing. Heat, shear, and/or an extreme pH, especially an acidic pH, tend to fully disrupt the starch granules and disperse the starch.

Cosmetics

Various materials have been used to thicken and emulsion stabilize cosmetic and hair care products. These materials include anionic derivatives of starch, xanthan gum, carboxymethylated starch or cellulose, and phosphorylated starch or cellulose. Currently, Carbopol resins, which are polyacrylic acid polymers produced by B.F. Goodrich, are the leading thickeners and emulsion stabilizers in the skin and hair care markets.

Unmodified starches are generally unsuitable in cosmetics because of their poor viscosity stability. Besides possessing the necessary rheological properties, cosmetic products with added thickeners and emulsion stabilizers must also have a suitable appearance and feeling on the skin.

There is a need in the cosmetic industry for non-chemically crosslinked starches which have the same functional properties as chemically-crosslinked starches.

SUMMARY OF THE INVENTION

The present invention is directed to the use of thermally-inhibited starches or flours in cosmetic skin care compositions which comprise a cosmetic vehicle and an effective thickening amount, emulsifying amount, and/or aesthetically-modifying amount of the thermally-inhibited starches or flours. Some thermally-inhibited starches and flours are used in aqueous-based skin care or hair formulations in a dispersed form as thickners and/or emulsifiers. Such starches and flours include thermally-inhibited unmodified starches and flours, as well as thermally-inhibited derivatized starches and flours, particularly those containing hydrophobic groups. Some thermally-inhibited starches and flours are used in the granular state as aesthetic-enhancing agents, e.g., in emulsion applications as a talc replacement. A particularly suitable starch for this aesthetic-enhancing property is a thermally-inhibited starch octenylsuccinate, preferably chemically crosslinked.

The present invention is also directed to the use of thermally-inhibited starches or flours in hair care compositions which comprise a hair care vehicle, an effective thickening amount, emulsifying amount, and/or aesthetically-modifying amount of the thermally-inhibited starches or flours.

In hair care compositions, most thermally-inhibited starches and flours are used in the dispersed state. However, thermally-inhibited starch octenylsuccinate, preferably crosslinked, can be used in the non-dispersed form in dry shampoos and pomades.

The starches and flours are thermally inhibited, without the addition of chemical reagents, in a heat treatment process that results in the starch or flour becoming and remaining inhibited. The starches and flours are referred to as "inhibited" or "thermally-inhibited (abbreviated "T-I"). When these thermally-inhibited starches and flours are dispersed and/or cooked in water, they exhibit the textural and viscosity properties characteristic of a chemically-crosslinked starch. The starch granules are more resistant to viscosity breakdown. This resistance to breakdown results in what is subjectively considered a non-cohesive or "short" textured paste, meaning that the gelatinized starch or flour tends to be salve-like and heavy in viscosity rather than runny or gummy.

When the thermally-inhibited starches and flours are non-pregelatinized granular starches or flours, the starches or flours exhibit an unchanged or reduced gelatinization temperature. In contrast, most annealed and heat/moisture treated starches show an increased gelatinization temperature. Chemically-crosslinked starches show an unchanged gelatinization temperature. It is believed the overall granular structure of the thermally-inhibited starches and flours has been altered.

The starches and flours that are substantially completely thermally inhibited will resist gelatinization. The starches and flours that are highly inhibited will gelatinize to a limited extent and show a continuing rise in viscosity but will not attain a peak viscosity. The starches and flours that are moderately inhibited will exhibit a lower peak viscosity and a lower percentage breakdown in viscosity compared to the same starch that is not inhibited. The starches and flours that are lightly inhibited will show a slight increase in peak viscosity and a lower percentage breakdown in viscosity compared to the same starch that is not inhibited.

The starches and flours are inhibited by a process which comprises the steps of dehydrating the starch or flour until it is anhydrous or substantially anhydrous and then heat treating the anhydrous or substantially anhydrous starch or flour at a temperature and for a period of time sufficient to inhibit the starch or flour. As used herein, "substantially anhydrous" means containing less than 1% moisture by weight. The dehydration may be a thermal dehydration or a non-thermal dehydration such alcohol extraction or freeze drying. An optional, but preferred, step is adjusting the pH of the starch or flour to neutral or greater prior to the dehydration step.

The amount of thermal inhibition required will depend on the reason the starch or flour is included in the cosmetic, as well as the particular processing conditions and cosmetic vehicles used to prepare the cosmetic. Cosmetics prepared with the thermally-inhibited starches and flours will possess viscosity stability, process tolerance such as resistance to heat, acid and shear, and improved texture.

Depending on the extent of the heat treatment, various levels of inhibition can be achieved. For example, lightly inhibited, higher viscosity products with little breakdown, as well as highly inhibited, low viscosity products with no breakdown, can be prepared by the thermal inhibition processes described herein.

Typically, if a highly inhibited starch or flour is used for improving the aesthetic properties, the amount of the starch or flour is about 0.3–90%, preferably 0.5–30%, by weight based on the weight of the cosmetic composition. Typically, if a lightly inhibited starch or flour is used for thickening (i.e., increasing viscosity) or emulsifying, the amount of the starch or flour is about 0.1–20%, preferably 0.3–5%, by weight based on the weight of the cosmetic composition.

Typical skin care compositions include shaving creams, lotions, mousses, creams, sunscreens, liquid makeups, lipsticks, dusting powders, pressed powders, topical spray powders, anti-perspirant sticks, roll-on anti-perspirants, after shave balms, powder eye shadows, and the like. The hand and body lotions may contain "actives", i.e., functional ingredients such as alpha-hydroxy acids, anti-fungal agents, sunscreen agents, moisturizing agents vitamins, and the like. They may be mineral oil-free moisturizing hand and body lotions, optionally containing a UV protection ingredient. The sunscreens may be surfactant-free.

Typical hair care compositions include gels, mousses, hair sprays, shampoos, hair styling aids, colorants, and the like. The thermally-inhibited starches and flours, preferably lightly inhibited, are used in shampoos, colorants, mousses, gels, or other hair styling aids as natural thickeners or fixatives. The thermally-inhibited starches or flours may be modified prior to or after the thermal inhibition to introduce emulsifying properties and used in shampoos, mousses, or other hair care products where emulsification is required.

DESCRIPTION OF THE PREFERRED EMBODIMENTS

All starches and flours are suitable for use herein. The thermally-inhibited starches and flours are used in these compositions for their thickening, emulsifying, or aesthetic properties, which will depend on the starch or flour base selected as well as its modification, e.g., derivitization to introduce emulsifying properties or crosslinking to introduce additional inhibition so that the starches do not swell during storage of the cosmetic composition. The thermally-inhibited starches and flours used herein are inert natural materials and, in addition to the thickening and/or stabilizing properties, they provide cosmetic formulations with excellent aesthetic properties related to skin feel and appearance. More significantly, the thermally-inhibited starches and flours are substantially sterilized and, if stored and maintained properly, have a significantly reduced microbial content.

The thermally-inhibited starches and flours can be derived from any native source. A "native" starch or flour is one as it is found in nature in unmodified form. Typical sources for the starches and flours are cereals, tubers, roots, legumes and fruits. The native source can be corn, white corn, pea, potato, sweet potato, banana, barley, wheat, rice, sago, amaranth, tapioca, sorghum, waxy maize, waxy tapioca, waxy pea, waxy wheat, waxy rice, waxy barley, waxy potato, waxy sorghum, high amylose starches containing greater than 40% amylose, and the like. Preferred starches are potato, corn, rice, oat, and waxy starches such as waxy maize, waxy tapioca, waxy rice, and waxy barley. The preferred flour is tapioca flour.

The thermal inhibition process may be carried out prior to or after other starch or flour reactions are used to modify starch or flour. The starches may be modified by conversion (i.e., acid-, enzyme-, and/or heat-conversion), oxidation, phosphorylation, etherification (e.g., by reaction with propylene oxide), esterification (e.g., by reaction with acetic anhydride or octenylsuccinic anhydride), and/or chemical crosslinking (e.g., by reaction with phosphorus oxychloride or sodium trimetaphosphate). The flours may be modified by bleaching or enzyme conversion. Procedures for modifying starches are described in the Chapter "Starch and Its Modification" by M. W. Rutenberg, pages 22–26 to 22–47, Handbook of Water Soluble Gums and Resins, R. L. Davidson, Editor (McGraw-Hill, Inc., New York, N.Y. 1980).

One of the preferred derivatized starches for use in preparing the thermally-inhibited starches with emulsifying properties are derivatives containing amino-multicarboxylate groups. The derivatives have the formula:

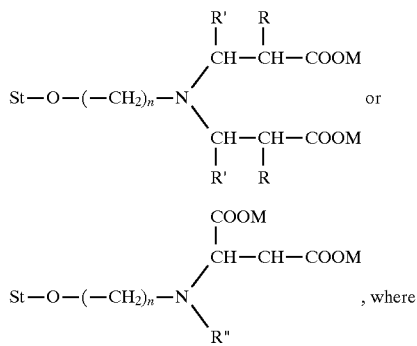

St—O represents a starch molecule or a modified starch molecule (where the hydrogen of a hydroxy group on an anhydroglucose unit has been replaced as shown); R is H or $CH_3$; R' is H, $CH_3$, or COOH; M is a cation such as H, an alkali metal, an alkaline earth metal, or ammonium; n is 2 or 3; and R" is H or a $C_1$–$C_{18}$ alkyl group. The derivatized starches are prepared by reacting an amino-multicarboxylic reagent (0.1–100% by weight based on the starch) with a starch base in an aqueous medium using either an aqueous slurry or an aqueous dispersion of the starch base. The reaction is carried out under alkaline conditions at a temperature of about 10°–95° C., preferably 20°–50° C., in the presence of salts if a granular starch is desired. The reaction time will vary from 0.2 to 24 hours. After completion of the reaction, the pH is adjusted to 3 to 9 and the starch is recovered as known in the art, which will depend upon whether a granular or non-granular starch is being prepared.

Native granular starches have a natural pH of about 5.0–6.5. When such starches are heated to temperatures above about 125° C. in the presence of water, acid hydrolysis (i.e., degradation) of the starch occurs. This degradation impedes or prevents inhibition. Therefore, the dehydration conditions need to be chosen so that degradation is minimized or avoided. Suitable conditions are thermally dehydrating at low temperatures and the starch's natural pH or thermally dehydrating at higher temperatures after increasing the pH of the starch to neutral or above. As used herein, "neutral" covers the range of pH values around pH 7 and is meant to include from about pH 6.5–7.5. A pH of at least 7 is preferred. More preferably, the pH is 7.5–10.5. The most preferred pH range is above 8 to below 10. At a pH above 12, gelatinization more easily occurs. Therefore, pH adjustments below 12 are more effective. It should be noted that the textural and viscosity benefits of the thermal inhibition process tend to be enhanced as the pH is increased, although higher pHs tend to increase browning of the starch or flour during the heat treating step.

To adjust the pH, the non-pregelatinized granular starch or flour is typically slurried in water or another aqueous medium, in a ratio of 1.5 to 2.0 parts of water to 1.0 part of starch or flour, and the pH is raised by the addition of any suitable base. Buffers, such as sodium phosphate, may be used to maintain the pH if needed. Alternatively, a solution of a base may be sprayed onto the powdered starch or flour until the starch or flour attains the desired pH, or an alkaline gas such as ammonia can be infused into the starch or flour. After the pH adjustment, the slurry is then either dewatered and dried, or dried directly, typically to a 2–15% moisture content. These drying procedures are to be distinguished from the thermal inhibition process steps in which the starch or flour is dehydrated to anhydrous or substantially anhydrous and then heat treated.

The starches or flours can be pregelatinized prior to or after the thermal inhibition process using methods known in the art. The amount of pregelatinization, and consequently, whether the starch will display a high or a low initial viscosity when dispersed in water, can be regulated by the pregelatinization procedure used, as is known in the art. The resulting pregelatinized starches are useful in applications where cold-water-soluble or cold-water-dispersible starches are used.

Pregelatinized granular starches and flours have retained their granular structure but lost their polarization crosses. They are pregelatinized in such a way that a majority of the starch granules are swollen, but remain intact. Exemplary processes for preparing pregelatinized granular starches are disclosed in U.S. Pat. No. 4,280,851 (issued Jul. 28, 1981 to E. Pitchon et al.), U.S. Pat. No. 4,465,702 (issued Aug. 14, 1984 to J. E. Eastman et al.), U.S. Pat. No. 5,037,929 (issued Aug. 6, 1991 to S. Rajagopalan), and U.S. Pat. No. 5,149,799 (issued Sep. 22, 1992 to Roger W. Rubens), the disclosures of which are incorporated by reference.

Pregelatinized non-granular starches and flours have also lost their polarization crosses and have become so swollen that the starches have lost their granular structure and broken into fragments. They can be prepared according to any of the known physical, chemical or thermal pregelatinization processes that destroy the granule such as drum drying, extrusion, or jet-cooking. See U.S. Pat. No. 1,516,512 (issued Nov. 25, 1924 to R. W. G. Stutzke); U.S. Pat. No. 1,901,109, (issued Mar. 14, 1933 to W. Maier); U.S. Pat. No. 2,314,459 (issued Mar. 23, 1943 to A. A. Salzburg; U.S. Pat. No. 2,582,198 (issued Jan. 8, 1957 to O. R. Ethridge); U.S. Pat. No. 2,805,966 (issued Sep. 10, 1957 to O. R. Ethridge); U.S. Pat. No. 2,919,214 (issued Dec. 29, 1959 to O. R. Ethridge); U.S. Pat. No. 2,940,876 (issued Jun. 14, 1960 to N. E. Elsas); U.S. Pat. No. 3,086,890 (issued Apr. 23, 1963 to A. Sarko et al.); U.S. Pat. No. 3,133,836 (issued May 19, 1964 to U. L. Winfrey); U.S. Pat. No. 3,137,592 (issued Jun. 16, 1964 to T. F. Pratzman et al.); U.S. Pat. No. 3,234,046 (issued Feb. 8, 1966 to G. R. Etchison); U.S. Pat. No. 3,607,394 (issued Sep. 21, 1971 to F. J. Germino); U.S. Pat.

No. 3,630,775 (issued Dec. 18, 1971 to A. A. Winkler); and U.S. Pat. No. 5,131,953 (issued Jul. 21, 1992 to J. J. Kasica et al.); the disclosures of which are incorporated by reference.

If the pregelatinization process is performed first and the pregelatinized starch or flour is granular, the pH is adjusted by slurrying the pregelatinized granular starch or flour in water in a ratio of 1.5–2.0 parts to 1.0 part starch, and optionally, the pH is adjusted to neutral or greater. In another embodiment, the slurry is simultaneously pregelatinized and dried and the dried, starch or flour is thermally inhibited. If the thermal inhibition process is performed first, the starch or flour is slurried in water, the pH of the starch or flour is adjusted to neutral or greater, and the starch or flour is dried to about 2–15% moisture. The dried starch or flour is then dehydrated and heat treated. The inhibited starch or flour is reslurried in water, optionally pH adjusted, and simultaneously pregelatinized and dried.

For non-granular pregelatinized starches or flours prepared by drum drying, the pH is raised by slurrying the starch or flour in water at 30–40% solids and adding a sufficient amount of a solution of a base until the desired pH is reached.

For non-granular pregelatinized starches or flours prepared by the continuous coupled jet-cooking/spray-drying process of U.S. Pat. No. 5,131,953 or the dual atomization/spray-drying process of U.S. Pat. No. 4,280,851, the starch or flour is slurred at 6–10% solids in water and the pH is adjusted to the desired pH by adding a sufficient amount of a solution of a base until the desired pH is reached.

Suitable bases for use in the pH adjustment step include, but are not limited to, sodium hydroxide, sodium carbonate, tetrasodium pyrophosphate, ammonium orthophosphate, disodium orthophosphate, trisodium phosphate, calcium carbonate, calcium hydroxide, potassium carbonate, and potassium hydroxide, and any other bases approved for use under the applicable regulatory laws. The preferred base is sodium carbonate. It may be possible to use bases not approved provided they can be washed from the starch or flour so that the final product conforms to good manufacturing practices for the desired end use.

A thermal dehydration is carried out by heating the starch or flour in a heating device for a time and at a temperature sufficient to reduce the moisture content to less than 1%, preferably 0%. Preferably, the temperatures used are 125° C. or less, more preferably 100°–120° C. The dehydrating temperature can be lower than 100° C., but a temperature of at least 100° C. will be more efficient for removing moisture.

Representative processes for carrying out a non-thermal dehydration include freeze drying or extracting the water from the starch or flour using a solvent, preferably a hydrophilic solvent, more preferably a hydrophilic solvent which forms an azeotropic mixture with water (e.g., ethanol).

For a laboratory scale dehydration with a solvent, the starch or flour (about 4–5% moisture) is placed in a Soxhlet thimble which is then placed in a Soxhlet apparatus. A suitable solvent is placed in the apparatus, heated to its reflux temperature, and refluxed for a time sufficient to dehydrate the starch or flour. Since during the refluxing the solvent is condensed onto the starch or flour, the starch or flour is exposed to a lower temperature than the solvent's boiling point. For example, during ethanol extraction the temperature of the starch is only about 40°–500° C. even though ethanol's boiling point is about 78° C. When ethanol is used as the solvent, the refluxing is continued for about 17 hours. The extracted starch or flour is removed from the thimble, spread out on a tray, and the excess solvent is allowed to flash off. The time required for ethanol to flash off is about 20–30 minutes. The dehydrated starch or flour is immediately placed in a suitable heating apparatus for the heat treatment. For a commercial scale dehydration any continuous extraction apparatus is suitable.

For dehydration by freeze drying, the starch or flour (4–5% moisture) is placed on a tray and put into a freeze dryer. A suitable bulk tray freeze dryer is available from FTS Systems of Stone Ridge, New York under the trademark Dura-Tap. The freeze dryer is run through a programmed cycle to remove the moisture. The temperature is held constant at about 20° C. and a vacuum is drawn to about 50 milliTorr (mT). The starch or flour is removed from the freeze dryer and immediately placed into a suitable heating apparatus for the heat treatment.

After it is dehydrated, the starch or flour is heat treated for a time and at a temperature sufficient to inhibit the starch or flour. The temperature required will depend upon the starch base, with waxy starches requiring a higher temperature. The preferred heating temperatures are greater than about 100° C. For practical purposes, the upper limit of the heat treating temperature is about 200° C. Typical temperatures are 120°–180° C., preferably 140°–160° C., most preferably 160° C. The temperature selected will depend upon the amount of inhibition desired and the rate at which it is to be achieved.

The time at the final heating temperature will depend upon the level of inhibition desired. When a conventional oven is used, the time ranges from 1 to 20 hours, typically 2 to 5 hours, usually 3.5 to 4.5 hours. When a fluidized bed is used, the times range from 0 minutes to 20 hours, typically 0.5 to 3.0 hours. Longer times are required at lower temperatures to obtain more inhibited starches.

For most applications, the thermal dehydrating and heat treating steps will be continuous and accomplished by the application of heat to the starch or flour beginning from ambient temperature. The moisture will be driven off during the heating and the starch or flour will become anhydrous or substantially anhydrous. Usually, at the initial levels of inhibition, the peak viscosities are higher than the peak viscosities of starches or flours heated for longer times, although there will be greater breakdown in viscosity from the peak viscosity. With continued heat treating, the peak viscosities are lower, but the viscosity breakdowns are less.

The process may be carried out as part of a continuous process involving the extraction of the starch from a plant material.

As will be seen in the following examples, the source of the starch or flour, initial pH, dehydrating conditions, heating time and temperature, and equipment used are all interrelated variables that affect the amount of inhibition.

The heating steps may be performed at normal pressures, under vacuum or under pressure, and may be accomplished by conventional means known in the art. The preferred method is by the application of dry heat in dry air or in an inert gaseous environment.

The heat treating step can be carried out in the same apparatus in which the thermal dehydration occurs. Most conveniently, the process is continuous with the thermal dehydration and heat treating occurring in the same apparatus, as when a fluidized bed reactor is used.

The dehydrating and heat treating apparatus can be any industrial ovens, conventional ovens, microwave ovens, dextrinizers, dryers, mixers and blenders equipped with heating devices and other types of heaters, provided that the apparatus is fitted with a vent to the atmosphere so that moisture does not accumulate and precipitate onto the starch or flour. The preferred apparatus is a fluidized bed. Preferably, the apparatus is equipped with a means for removing water vapor, such as, a vacuum or a blower to sweep air or the fluidizing gas from the head-space of the fluidized bed. Suitable fluidizing gases are air and nitrogen. Dry air is preferred. For safety reasons, it is preferable to use a gas containing less than 12% oxygen.

Superior inhibited starches and flours having high viscosities with low percentage breakdown in viscosity are obtained in shorter times in the fluidized bed reactor than can be achieved using other conventional heating ovens or dryers.

Optional steps can be carried out to improve the color and/or flavor. They include washing the starch or flour with water and/or removing protein and/or lipid from the starch or flour prior to the dehydrating step and/or after the heat treating step. A bleaching agent (e.g., sodium chlorite) or an alkali can be used for the protein and/or lipid removal.

The starches or flours may be inhibited individually or more than one may be inhibited at the same time. They may be inhibited in the presence of other materials or ingredients that would not interfere with the thermal inhibition process or alter the properties of the starch or flour product.

Following the thermal inhibition step, the resulting starches may be screened to the desired particle size. If the starch is a non-pregelatinized granular starch, the starch can be slurried in water, washed, filtered, dried, and bleached. If the starch is a granular pregelatinized starch, the starch can be washed by any known methods that will maintain granular integrity.

If desired, the pH may be adjusted.

The thermally-inhibited starches and flours can be used wherever starches and flours are conventionally used in cosmetics, e.g., as thickeners, emulsifiers, and aesthetic modifiers in skin and hair care compositions.

Lotions, such as hand and body lotions and sunscreens, typically contain oil(s), water, emulsifier(s), and optionally active ingredient(s) (e.g., sunscreen or alpha-hydroxy acid), and/or pigments. Powders typically contain a covering powder and a liquid or dry binder. A waxy matrix is used for creamy powdered cosmetics such as eye shadow and lipstick. Antiperspirants generally contain an aluminum salt as the active ingredient, with a roll-on containing a volatile silicone in a suspension or emulsion, with a stick containing a low melting wax base and optionally a silicone, and with an aerosol powder-oil suspension containing a propellant. A shaving cream typically contains a fatty acid, surfactant, lubricant and optionally a propellant or humectant.

Shampoos typically contain water, primary and secondary surfactants, preservatives, and optionally conditioners, opacifiers, chelating agents, fragrances, color, salt and/or polymeric thickeners. Conditioners typically contain water, preservative, and a film forming compound or cationic polymer.

Oxidative hair dyes typically contain dye intermediate(s), alkalinity source(s), solvent(s), surfactant(s), reducing agent (s), water, and other optional ingredients as the dye base and hydrogen peroxide, stabilizer(s), surfactant(s), water, and other optional ingredients in the developer.

Thickeners and/or suspending agents are preferably added to the above cosmetics.

Skin and hair care compositions may involve different media or systems and will comprise a suitable cosmetic vehicle or base for the composition. Skin and hair care vehicles are known in the art. They include emulsions, aqueous systems, solvent systems, mixtures of an aqueous system and a solvent system, aerosols, semi-solids and the like.

Emulsions are the preferred vehicle or base for cosmetic compositions such as skin care creams and lotions. These emulsions, which comprise water-based and oil-based phases, may be oil-in-water emulsions having oil as the dispersed phase and water as the continuous phase or they may be water-in-oil emulsions having water dispersed in the oil which is the continuous phase.

The oil phase, which may comprise from about 10 to 90% by weight of the composition, is typically made up of cosmetically acceptable or conventional oily substances such as oils, waxes and emulsifiers. Compounds which can be included in the oil phase are typically mineral, animal and vegetable oils and fats, synthetic esters, fatty acids, aliphatic alcohols, higher fatty alcohols, alkyl amines, waxes, so called mineral fats and oils such as paraffin oil, petrolatum, ceresin, silicone oils and silicone fats.

The water phase may comprise from about 10 to 90% by weight of the composition and can include water and water-soluble components such as alkali thickeners, alkanolamines, polyhydric alcohols, preservatives, alpha-hydroxy acids, or other water soluble ingredients.

The emulsions include one or more emulsifiers which usually are contained in the oil phase but, in some instances, depending on the type, may be in the water phase. The aminomulticarboxylate starch derivatives (e.g., CEPA derivatives) described previously may be used to stabilize the emulsion or to replace secondary emulsifiers. Ionic or non-ionic emulsifiers which can be used are well known and constitute a large group of conventional and commercially available products. They are often characterized by their hydrophilic-lipophilic balance (HLB). Oil-in-water (OW) emulsifying agents typically have an HLB of more than 6.0 and produce emulsions in which the continuous phase is hydrophilic and such agents are generally dispersible in water. Emulsifiers of this type include PEG 300 distearate, sorbitan monolaurate, and triethanolamine stearate. Water-in-oil (W/O) emulsifiers usually have an HLB of less than 6.0, preferably below 5, and produce emulsions in which the continuous phase is lipophilic. Such emulsifiers include lanolin alcohols, ethylene glycol monostearate, sorbitan monooleate and PEG 200 dilaurate. Emulsifiers with HLB's of between 5 and 7 may function as either W/O or O/W emulsifiers depending on how they are used.

The amount of emulsifier used, including the thermally-inhibited aminomulticarboxylate starch derivatives, can vary depending on the cosmetic system and will be an effective emulsifying amount. Typically, the amount can vary from about 0.1–25%, preferably about 1–10%, by weight of the composition.

Various other ingredients and additives may be included in the oil and/or water phases of skin care emulsions. These include emollients, humectants, thickening agents, UV-light inhibitors, preservatives, pigments, dyes, colorants, alpha-hydroxy acids, aesthetic enhancers, perfumes and fragrances, film formers (water proofing agents), antiseptics, antifungal and antimicrobial medicaments, and solvents. Effective amounts of one or more of these and other active and functional ingredients are generally used and they can total from about 1 to 25%, typically about 0.1–15%, by weight of the composition.

Other cosmetic compositions involve aqueous or solvent systems wherein the added components are soluble or dispersible therein.

The aqueous system will comprise the selected thermally-inhibited starches of flours, additives, active and functional ingredients, with the balance being water. A propellant is optional. Generally, an aqueous system will comprise from about 10–99.8%, preferably about 50–80%, water; from about 0.1–20%, preferably about 0.3–5% thermally-inhibited starch; from about 0.1–25%, preferably about 0.1–15%, other ingredients; and up to about 50%, preferably up to about 30%, propellant; the percentages are by weight. Compositions of this type include topical sprays and products containing fragrances and antimicrobial agents. The topical sprays include aerosol sprays or products containing a propellant. While any of the known propellants may be used in the compositions of this invention, preferred propellants include the non-halogenated hydrocarbons, particularly the lower boiling hydrocarbons such as $C_3$–$C_6$ straight and branched chain hydrocarbons (e.g., propane, butane, and/or isobutane), ethers (e.g., dimethyl ether), hydrofluorocarbons, and compressed gases (e.g., nitrogen and carbon dioxide).

The use of a solvent system as the vehicle or base involves other cosmetic compositions containing selected granular thermally-inhibited starches for aesthetic reasons, not for thickening or emulsifying. The solvent system will contain the thermally-inhibited starch, additives and active and functional ingredients, optionally a propellant, with the balance being the solvent. The solvent may be any of the known organic solvents which may solubilize or disperse the ingredients typically used in the skin care composition. Typical solvents include aliphatic alcohols, esters, ethers, ketones, amines and hydrocarbons including aromatic, nitrated and chlorinated hydrocarbons. Particularly preferred organic solvents are the lower aliphatic alcohols such as the $C_1$–$C_3$ alcohols, preferably ethanol. Generally the solvent system will comprise from about 25–99.8%, preferably about 50–80%, solvent; about 0.1–20%, preferably about 0.3–5%, thermally-inhibited starch; about 0.1–25%, preferably about 0.1–15%, other ingredients; and up to about 75%, preferably about 35%, propellant; the percentages are by weight.

Additives and other ingredients which may be included in either the aqueous- or solvent-based systems are the same as those described above for the emulsion- and oil-based systems. Propellants which may be included in the solvent systems are the same as those described above for the aqueous systems.

Additionally, a mixture of aqueous and solvent systems may be used wherein the water and solvent, especially alcohols, are combined along with the ingredients, e.g., the thermally-inhibited starch or flour, additives, and optional propellant. Such a composition will comprise about 25–99.8 wt. %, preferably about 50–80 wt. %, of the combined water and solvent, along with the ingredients described above.

The thermally-inhibited starches and flours used in cosmetic compositions in accordance with this invention will comprise an effective thickening, emulsion stabilizing, or aesthetically-modifying amount. More particularly, the starches or flours will comprise from about 0.1–20%, preferably about 0.3–5%, by weight of the cosmetic composition. The conditions used for the inhibition of representative selected starches are discussed below.

An unmodified starch, e.g., potato starch, will be adjusted to pH 7.5–11, preferably pH 8–10, dehydrated, and heat treated at 100°–160° C., preferably 120°–150° C., for a time sufficient to thermally inhibit the starch but still allow it to cook out and thicken the cosmetic compositions.

The starches (e.g., potato or corn) can be derivatized to introduce hydrophobic groups (e.g., by reaction with octenylsus cinic anhydride, dodecenylsuccinic anhydride, 3-chloro-2-hydroxypropyl dimethyl dodecyl chloride, or like hydrophobic reagents), dehydrated, and heat treated at pH 7–11, preferably 9–9.5, at 120°–180° C., preferably 150°–170° C., for a time sufficient to inhibit the starch but still allow it to cook out and thicken and/or emulsify the cosmetic composition. If a highly inhibited starch is required, a longer heating time at a higher temperature and a higher pH is used. If a lightly inhibited starch is required, a short heating time at a lower temperature is used.

The starches modified with aminomulticarboxylic acids, e.g., 2-chloroethynlaminodipropionic acid (CEPA), are dehydrated and heat treated at pH 7.5–9.5, preferably 8–8.5, for a time and at a temperature sufficient to lightly inhibit the starches but still allow them to cook out and thicken and/or emulsify the cosmetic compositions. This requires the use of low temperatures, e.g., (110°–140° C.) and short heating times (e.g., 30 minutes) or preferably no holding time after the final heating temperature is reached.

Preparation of cosmetic emulsion compositions typically involves combining the oil-soluble ingredients in one vessel and heating the mixture to, e.g., 75°–80° C., and combining the water-soluble ingredients in another vessel and heating the mixture to, e.g., 75°–80° C. Depending on whether oil in water (O/W) or water in oil (W/O) emulsions are being prepared, the warmed inner phase is then slowly added to the outer phase with agitation.

Sample Preparation

Unless indicated otherwise, all the starches and flours used were provided by National Starch and Chemical Company of Bridgewater, N.J.

The controls for the test samples were from the same native source as the test samples, were unmodified or modified in the same manner as the test samples, and were at the same pH unless otherwise indicated.

All starches and flours, both test and control samples, were prepared and tested individually.

The pH of the samples was raised by slurrying the starch or flour in water at 30–40% solids and adding a sufficient amount of a 5% sodium carbonate solution until the desired pH was reached.

Measurements of pH, either on samples before or after the thermal inhibition steps, were made on samples consisting of one part starch or flour to four parts water.

After the pH adjustments, if any, all non-pregelatinized granular samples were spray-dried or flash-dried as conventional in the art (without gelatinization) to about 2–15% moisture.

After the pH adjustment, if any, slurries of the starches to be pregelatinized to granular pregelatinized starches were introduced into a pilot spray dryer, Type 1-KA#4F, from APV Crepaco, Inc., Dryer Division, Attleboro Falls, Mass., using a spray nozzle, Type 1/2J, from Spraying Systems Company of Wheaton, Ill. The spray nozzle had the following configurations: fluid cap 251376, air cap 4691312. The low initial cold viscosity samples were sprayed at a steam-:starch ratio of 3.5–4.5:1, and the high initial cold viscosity samples were sprayed at a steam:starch ratio of 5.5–6.5:1. Moisture content of all pregelatinized samples after spray drying and before the dehydration step in the thermal inhibition process was 4–10%.

For the samples pregelatinized by drum drying the pH was raised by slurrying the starch or flour in water at 30–40% solids and adding a sufficient amount of a 5% sodium carbonate solution until the desired pH was reached. A single steam-heated steel drum at about 142°–145° C. was used for the drum drying.

For the samples pregelatinized by the continuous coupled jet-cooking/spray-drying process of U.S. Pat. No. 5,131,953 or the dual atomization/spray-drying process of U.S. Pat. No. 4,280,851, the starch or flour was slurred at 6–10% solids in water and the pH was adjusted to the desired pH by adding a sufficient amount of 5% sodium carbonate solution until the desired pH was reached.

Except where a conventional oven or dextrinizer is specified, the test samples were dehydrated and heat treated in a fluidized bed reactor, model number FDR-100, manufactured by Procedyne Corporation of New Brunswick, N.J. The cross-sectional area of the fluidized bed reactor was 0.05 sq meter. The starting bed height was 0.3–0.8 meter, but usually 0.77 meter. The fluidizing gas was air except where otherwise indicated. When granular non-pregelatinized starches were being heat treated, the gas was used at a velocity of 5–15 meter/min. When pregelatinized granular starches were being heat treated, the gas was used at a velocity of 15–21 meter/min. The side walls of the reactor were heated with hot oil, and the fluidizing gas was heated with an electric heater. The samples were loaded into the reactor and then the fluidizing gas was introduced, or the samples were loaded while the fluidizing gas was being introduced. No difference was noted in the samples in the order of loading. Unless otherwise specified, the samples were brought from ambient temperature up to no more than 125° C. until the samples became anhydrous and were further heated to the specified heat treating temperatures. When the heating temperature was 160° C, the time to reach that temperature was less than three hours.

The moisture level of the samples at the final heating temperature was 0%, except where otherwise stated. Portions of the samples were removed and tested for inhibition at the temperatures and times indicated in the tables.

Unless specified otherwise, the samples were tested for inhibition using the following Brabender Procedures.

Brabender Procedure—Non-Pregelatinized Granular Starches

Unless other stated, the following Brabender procedure was used. All samples, except for corn, tapioca and waxy rice flour, were slurried in a sufficient amount of distilled water to give a 5% anhydrous solids starch slurry. Corn, tapioca, and waxy rice flour were slurried at 6.3% anhydrous solids. The pH was adjusted to pH 3.0 with a sodium citrate, citric acid buffer and the slurry was introduced into the sample cup of a Brabender VISCO/Amylo/GRAPH (manufactured by C. W. Brabender Instruments, Inc., Hackensack, N.J.) fitted with a 350 cm/gram cartridge. The VISCO\Amylo\GRAPH records the torque required to balance the viscosity that develops when a starch slurry is subjected to a programmed heating cycle. The record consists of a curve tracing the viscosity through the heating cycle in arbitrary units of measurement termed Brabender Units (BU).

The starch slurry is heated rapidly to 92° C. and held for 10 minutes. The peak viscosity and viscosity ten minutes after peak viscosity were recorded in Brabender Units (BU). The percentage breakdown in viscosity (±2%) was calculated according to the formula:

$$\% \text{ Breakdown} = \frac{\text{peak} - (\text{peak} + 10')}{\text{peak}} \times 100,$$

where "peak" is the peak viscosity in Brabender units, and "(peak+10')" is the viscosity in Brabender Units at ten minutes after peak viscosity. If no peak viscosity was reached, i.e., the data indicate a rising (ris.) curve or a flat curve, the viscosity at 92° C. and the viscosity at 30 minutes after attaining 92° C. were recorded.

Using data from the Brabender curves, inhibition was determined to be present if, when dispersed at 5% or 6.3% solids in water at 92°–95° C. and pH 3, during the Brabender heating cycle, the Brabender data showed (i) no or almost no viscosity, indicating the starch was so inhibited it did not gelatinize or strongly resisted gelatinization; (ii) a continuous rising viscosity with no peak viscosity, indicating the starch was highly inhibited and gelatinized to a limited extent; (iii) a lower peak viscosity and a lower percentage breakdown in viscosity from peak viscosity compared to a control, indicating a moderate level of inhibition; or (iv) a slight increase in peak viscosity and a lower percentage breakdown compared to a control, indicating a low level of inhibition.

Characterization Of Inhibition of Non-Pregelatinized Granular Starches By Brabender Curves Characterization of a thermally-inhibited starch is made more conclusively by reference to a measurement of its Brabender viscosity after it is dispersed in water and gelatinized.

For non-inhibited starches, the cooking cycle passes through the initiation of viscosity, usually at about 60°–70° C., the development of a peak viscosity in the range of 67°–95° C., and any breakdown in viscosity when the starch is held at an elevated temperature, usually 92°–95° C.

Inhibited starches will show a Brabender curve different from the curve of the same starch that has not been inhibited (hereinafter the control starch). At low levels of inhibition, an inhibited starch will attain a peak viscosity somewhat higher than the peak viscosity of the control, and there may be no decrease in percentage breakdown in viscosity compared to the control. As the amount of inhibition increases, the peak viscosity and the breakdown in viscosity decrease. At high levels of inhibition, the rate of gelatinization and swelling of the granules decreases, the peak viscosity disappears, and with prolonged cooking the Brabender trace becomes a rising curve indicating a slow continuing increase in viscosity. At very high levels of inhibition, starch granules no longer gelatinize, and the Brabender curve remains flat.

Brabender Procedure—Pregelatinized Granular and Non-Granular Starches

The pregelatinized thermally-inhibited starch to be tested was slurried in a sufficient amount of distilled water to give a 4.6% anhydrous solids starch slurry at pH 3 as follows: 132.75 g sucrose, 26.55 g starch, 10.8 g acetic acid, and 405.9 g water were mixed for three minutes in a standard home Mixmaster at setting #1. The slurry was then introduced to the sample cup of a Brabender VISCO/Amylo/GRAPH fitted with a 350 cm/gram cartridge and the viscosity measured as the slurry was heated to 30° C. and held for 10 minutes. The viscosity at 30° C. and 10 minutes after hold at 30° C. were recorded. The viscosity data at these temperatures are a measurement of the extent of pregelatinization. The higher the viscosity at 30° C., the grater the extent of granular swelling and hydration during the pregelatinization process.

Heating was continued to 95° C. and held at that temperature for 10 minutes.

The peak viscosity and viscosity 10 minutes after 95° C. were recorded in Brabender Units (BU). The percentage breakdown was calculated using the previous formula:

If no peak viscosity was reached, that is, the data indicated a rising curve or a flat curve, the viscosity at 95° C. and the viscosity at 10 minutes after attaining 95° C. were recorded.

Characterization of Inhibition of Pregelatinized Granular Starches by Brabender Curves As discussed above, characterization of a thermally-inhibited starch is made more conclusively by reference to a measurement of its viscosity after it is dispersed in water and gelatinized using the instrument described above.

For pregelatinized granular starches, the level of viscosity when dispersed in cold water will be dependent on the extent to which the starch was initially cooked out during the pregelatinization process. If the granules were not fully swollen and hydrated during pregelatinization, gelatinization will continue when the starch is dispersed in water and heated. Inhibition was determined by a measurement of the starch viscosity when the starch was dispersed at 4.6% solids in water at pH 3 and heated to 95° C.

When the pregelatinized granular starch had a high initial cold viscosity, meaning it was highly cooked out in the pregelatinization process, the resulting Brabender traces will be as follows: for a highly inhibited that the starch, the trace will be a flat curve, indicating that the starch is already very swollen and is so inhibited starch it is resisting any further gelatinization or the trace will be a rising curve, indicating that further gelatinization is occurring at a slow rate and to a limited extent; for a less inhibited starch, the trace will he a dropping curve, indicating that some of the granules are fragmenting, but the overall breakdown in viscosity will be lower than that for a non-inhibited control or the trace will show a second peak but the breakdown in viscosity will be lower than that for a non-inhibited control.

When the pregelatinized starch had a low initial cold viscosity, meaning it was not highly cooked out in the pregelatinization process and more cooking is needed to reach the initial peak viscosity, the resulting Brabender traces will be as follows: for a highly inhibited starch, the trace will be a rising curve, indicating that further gelatinization is occurring at a slow rate and to a limited extent; for a less inhibited starch, the trace will show a peak viscosity as gelatinization occurs and then a drop in viscosity, but with a lower percentage breakdown in viscosity than for a non-inhibited control.

If no peak viscosity was reached, that is, the data indicated a rising curve or a flat curve, the viscosity at 95° C. and the viscosity at 10 minutes after attaining 95° C. were recorded.

Characterization of Inhibition of Pregelatinized Non-Granular Starches by Brabender Curves The resulting Brabender traces will be as follows: for a highly inhibited starch the trace will be flat, indicating that the starch is so inhibited that it is resisting any further gelatinization or the trace will be a rising curve, indicating that further gelatinization is occurring at a slow rate and to a limited extent; for a less inhibited starch, the trace will show a dropping curve, but the overall breakdown in viscosity from the peak viscosity will be lower than that for a non-inhibited control.

Characterization of Inhibition by Cooks

A dry blend of 7 g of starch or flour (anhydrous basis) and 14 g of sugar were added to 91 ml of water in a Waring blender cup at low speed, then transferred to a cook-up beaker, allowed to stand for 10 minutes, and then evaluated for viscosity, color, clarity and texture.

Some of the granular non-pregelatinized starch samples were tested for pasting temperature and/or gelatinization temperature using the following procedures.

Rapid Visco Analyzer (RVA)

This test is used to determine the onset of gelatinization, i.e., the pasting temperature. The onset of gelatinization is indicated by an increase in the viscosity of the starch slurry as the starch granules begin to swell.

A 5 g starch sample (anhydrous basis) is placed in the analysis cup of a Model RVA-4 Analyzer and slurried in water at 20% solids. The total charge is 25 g. The cup is placed into the analyzer, rotated at 160 rpm, and heated from an initial temperature of 50° C. up to a final temperature of 80° C. at a rate of 3° C./minute. A plot is generated showing time, temperature, and viscosity in centipoises (cP). The pasting temperature is the temperature at which the viscosity reaches 500 cP. Both pasting temperature and pasting time are recorded.

Differential Scanning Calorimetry (DSC)

This test provides a quantitative measurement of the enthalapy ($\Delta H$) of the energy transformation that occurs during the gelatinization of the starch granule. The peak temperature and time required for gelatinization are recorded. A Perkin-Elmer DSC-4 differential scanning calorimeter with data station and large volume high pressure sample cells is used. The cells are prepared by weighing accurately 10 mg of starch (dry basis) and the appropriate amount of distilled water to approximately equal 40 mg of total water weight (moisture of starch and distilled water). The cells are then sealed and allowed to equilibrate overnight at 4° C. before being scanned at from 25°–150° C. at the rate of 10° C./minute. An empty cell is used as the blank.

Angle Of Repose Determination

This test measure the flow properties of the starch or flour. A large sheet of heavy Kraft paper (about 6 ft. square) is secured to a flat, level surface with masking tape. Two rings (3 in. and 4 in. in diameter) are clamped onto a ring stand (6×9 in. base and 24 in. rod) in such a way that the base faces in the opposite direction from the rings. The small ring is placed above the larger ring. To keep the funnels stationary, 1 in. pieces of heavy walled vacuum tubing ($\frac{1}{4}$ in. base by $\frac{3}{16}$ in. wall) are cut lengthwise through one wall and fitted equidistantly at 3 locations on each ring. A chemical funnel having a 100 mm top interior diameter (ID) (Kimax 58) is modified by removing the existing stem and annealing a 8 mm I.D. glass tubing 85 mm in length as the stem. The modified funnel is placed in the large ring and the height is adjusted so that the orifice of the funnel is 1±0.1 cm above the paper. A powder funnel having a 60 mm top I.D. and 13 mm stem I.D. (Kimax 29020-04) is placed in the small ring and the ring is lowered as far as possible, i.e., until the clamps meet. The small funnel should be centered above the large funnel with the orifice of the large funnel stem parallel to the paper. Approximately 50 g of the sample to be tested are slowly added to the powder funnel while gently placing the top of an index finger over the orifice of the large funnel so that any sample which overflows the powder funnel does not flow out of the large funnel. The finger is slowly removed from the orifice while taking care not to move the funnel and allow the sample to flow onto the paper. Flow will cease when the top of the pile reaches the orifice of the funnel stem. With a pencil, the circumference of the sample pile is traced as accurately as possible without disturbing the sample. The sample is removed and the radius of the pile is measured. Each sample is run in triplicate. The test is repeated if the funnel stem becomes clogged before the pile meets the funnel orifice or if the pile is disturbed in any way. The funnels are cleaned after each run.

The average radius of the sample pile is calculated and the angle of repose is determined using the following formula:

$$\text{Tangent (angle of repose)} = \frac{\text{height of funnel orifice}}{\text{average radius of pile}}$$

Brookfield Viscometer Procedure

Test samples are measured using a Model RVT Brookfield Viscometer and the appropriate spindle (the spindle is selected based on the anticipated viscosity of the material). The test sample, usually a cooked starch paste, is placed in position and the spindle is lowered into the sample to the appropriate height. The viscometer is turned on and the spindle is rotated at a constant speed (e.g., 10 or 20 rpm) for at least 3 revolutions before a reading is taken. Using the appropriate conversion factors, the viscosity (in centipoises) of the sample is recorded.

The following examples will more fully illustrate the embodiments of the invention. In the examples, all parts are given by weight and temperature are in degrees Celsius unless otherwise noted. The thermally inhibited starches and controls in the following examples were prepared as described above and are defined by textural characteristics or in relation to data taken from Brabender curves using the above described procedures. The thermally-inhibited starches and flours are referred to as "T-I" starches and flours and the conditions used for their preparation (i.e., pH to which the starch is adjusted and heat treatment temperature and time at that temperature are included in parenthesis (pH; temperature/hold time at that temperature). All pH adjustments are done with sodium carbonate unless specified otherwise. Unless otherwise specified, the thermally-inhibited starches and flours referred to as "granular" starches are non-pregelatinized granular starches and flours.

In the first three examples, the moisture indicated is the moisture of the starch before the dehydration and heat treating steps. As indicated above, as the starches were brought from ambient temperature up to the heating temperature, the starches became anhydrous or substantially anhydrous.

In the tables the abbreviations "sl.", "mod.", "v.", "ris." and "N.D." stand for slight or slightly, moderate or moderately, heavy, rising, and not determined.

EXAMPLE 1

This example illustrates the preparation of the starches of this invention from a commercial granular waxy maize base starch by the heat treatment process of this invention.

Processing conditions and their effects on viscosity and texture of waxy maize starch are set forth in the Tables below.

To obtain a heat-stable, non-cohesive thickener, samples of granular starch were slurried in 1.5 parts of water, the pH of the slurry was adjusted with the addition of a 5% $Na_2CO_3$ solution and the slurry was agitated for 1 hour, then filtered, dried, and ground. The dry starch samples (150 g) were placed into an aluminum foil pan (4"×5"×1½") and heated in a conventional oven under the conditions described below. Brabender viscosity measurements demonstrated that the most heat-stable starches were obtained by heating at 160° C. and a pH of at least 8.0 for about 3.5 to 6.0 hours.

| | Process Variables | | | Cold Evaluation of Gelatinized Samples[d,e] | |
|---|---|---|---|---|---|
| | | Heating - 160° C. | | | |
| Waxy Maize[a] | pH | Moisture (%) | Time (hrs.) | Viscosity | Texture |
| 1 | 6.0 | 10.9 | 2 | heavy to v. heavy | cohesive |
| 2 | 6.0 | 10.9 | 4 | thin to mod. | — |
| 3 | 8.2 | 10.6 | 3.5 | heavy to v. heavy | cohesive, less than unmodified control |
| 4 | 8.2 | 10.6 | 4 | heavy to v. heavy | sl. to mod. cohesive |
| 5 | 8.2 | 10.6 | 4.5 | heavy | non-cohesive |
| 6 | 8.2 | 10.6 | 5.5 | heavy, thinnest | non-cohesive |
| 7 | 8.2 | 10.6 | 6 | mod. heavy | non-cohesive |
| unmodified[b] | — | — | — | v. heavy | cohesive |
| cross-linked control[c] | — | — | — | v. heavy | non-cohesive |

[a]All samples were commercial samples of granular waxy maize starch obtained from National Starch and Chemical Company, Bridgewater, New Jersey.
[b]The unmodified control was a commercial granular waxy maize starch obtained from National Starch and Chemical Company, Bridgewater, New Jersey.
[c]The modified control was a commercial cross-linked, (phosphorous oxychloride treated) granular waxy maize starch obtained from National Starch and Chemical Company, Bridgewater, New Jersey.
[d]Samples were cooked by slurrying 7.0 g of starch (at 12% moisture) in 91 mls water at neutral pHs and heating the starch slurry for 20 minutes in a boiling water bath.
[e]The cold evaluation was carried out at 25° C.

Brabender Evaluation

| | Process Variables | | | Brabender Viscosity[b] (BU) | |
|---|---|---|---|---|---|
| Waxy Maize[a] | pH | Heating Temp. (°C.) | Time (hrs.) | Peak Viscosity | Viscosity at 95° C./ 20 mins. |
| 3 | 8.2 | 160 | 3.5 | 985 | 830 |
| 4 | 8.2 | 160 | 4.0 | 805 | 685 |
| 5 | 8.2 | 160 | 4.5 | 640 | 635 |
| 6 | 8.2 | 160 | 5.5 | 575 | 570 |
| Unmodified control | — | none | none | 1640 | 630 |
| 1 | 6.0 | 160 | 2.0 | 1055 | 560 |
| 2 | 6.0 | 160 | 4.0 | 140 | 80 |

[a]See prior table for a description of samples.
[b]In the Brabender procedure, a sample containing 5.4% anhydrous solids of starch dispersed in water was heated rapidly to 50° C., then the heat was increased by 1.5° C. per minute to 95° C, and held for 20 minutes.

EXAMPLE 2

This example illustrates that a variety of granular starches may be processed by the method of this invention to provide a non-cohesive thickener with properties similar to chemically crosslinked starches.

Processing conditions and their effects on the viscosity and texture of waxy barley, tapioca, V.O. hybrid and waxy rice starches are set forth in the tables below.

| | Process Variables | | | Cold Evaluation of | |
|---|---|---|---|---|---|
| | Heating - 160° C. | | | | |
| Sample[a] | pH | Moisture (%) | Time (hrs.) | Gelatinized Sample[b] Viscosity/Texture | |
| Waxy Barley Starch | | | | | |
| 1 | 8.7 | 8.5 | 1.5 | heavy | cohesive |
| 2 | 8.7 | 8.5 | 2.5 | heavy | sl. mod. cohesive |
| 3 | 8.7 | 8.5 | 3.5 | mod. heavy to heavy | non-cohesive |
| 4 | 5.2 | 10.8 | 1.5 | thin | — |
| 5 | 5.2 | 10.8 | 2.5 | thin/thinnest | — |
| Waxy Barley Control | | | 0 | heavy | cohesive |
| Tapioca Starch | | | | | |
| 6 | 8.8 | 10.3 | 2 | heavy to v. heavy | cohesive |
| 7 | 8.8 | 10.3 | 3 | heavy to v. heavy | cohesive/less than Sample 6 |
| 8 | 8.8 | 10.3 | 4 | heavy to v. heavy | sl. cohesive to sl. lumpy |
| 9 | 8.8 | 10.3 | 5 | heavy | non-cohesive to lumpy |
| Tapioca Control | | | 0 | v. heavy | cohesive |
| 10 | 5.5 | 10.9 | 3 | mod. heavy | — |
| Waxy Rice Starch | | | | | |
| Waxy Rice Control | | | 0 | v. heavy | cohesive |
| 1 | 9.1 | 9.0 | 2 | v. heavy | cohesive |
| 2 | 9.1 | 9.0 | 3 | heavy | sl. cohesive |
| 3 | 9.1 | 9.0 | 4 | heavy | sl. cohesive |
| 4 | 9.1 | 9.0 | 5 | mod. heavy to heavy | non-cohesive |

[a]Tapioca starch samples were commercial granular starch obtained from National Starch and Chemical Company, Bridgewater, New Jersey. Waxy barley starch samples were commercial granular starch obtained from AlKo, Finland. Waxy rice starch samples were commercial granular starch obtained from Mitsubishi Corporation, Japan.
[b]Samples were cooked by slurring 7.5 g of starch at 12% moisture in 100 mls of water and heating the starch slurry for 20 minutes in a boiling water bath.

| | Process Variables | | | Cold Evaluation of | |
|---|---|---|---|---|---|
| | Heating - 160° C. | | | | |
| Sample[a] | pH | Moisture (%) | Time (hrs.) | Gelatinized Sample[b] Viscosity/Texture | |
| V.O. Hybrid Starch | | | | | |
| 1 | 8.7 | 10.5 | 2.0 | heavy | cohesive v. sl. less than control |
| 2 | 8.7 | 10.5 | 3.0 | heavy | sl. mod. cohesive |
| 3 | 8.7 | 10.5 | 4.0 | mod. heavy to heavy | smooth, very sl. cohesive |
| 4 | 8.7 | 10.5 | 5.0 | mod. heavy | smooth, short, non-cohesive |
| 5 | 8.7 | 10.5 | 6.0 | moderate | smooth, short, non-cohesive |
| V.O. Hybrid Control | 5.9 | 11.4 | 0 | heavy | cohesive |

[a]V.O. hybrid starch samples were granular starches obtained from National Starch and Chemical Company, Bridgewater, New Jersey.
[b]Samples were cooked by slurrying 7.5 g of starch at 12% moisture in 100 mls of water and heating the starch slurry for 20 minutes in a boiling water bath.

The viscosity and texture evaluation results show that a non-cohesive, heat-stable starch thickener may be prepared from waxy barley, V.O. hybrid, tapioca and waxy rice starches by the process of this invention. The amount of inhibition (non-cohesive, thickening character in cooked aqueous dispersion) increased with increasing time of heat treatment.

EXAMPLE 3

This example illustrates the effects of temperature, the pH, and starch moisture content on the viscosity and texture of the treated starch.

Part A

A waxy maize starch sample (100 g) containing 20.4% moisture was heated in an oven at 100° C. for 16 hours in a sealed glass jar. A second sample was heated for 4 hours and a third sample was heated for 7 hours under the same conditions. The product viscosity and texture were compared to a 12.1% moisture granular waxy maize starch control using the cook evaluation method of Example 1.

The results are shown below.

| | | Effect of Process Moisture | | |
|---|---|---|---|---|
| | | Process Variables[b] Heat Time | Cold Evaluation of Gelatinized Starch[c] | |
| Sample[a] | | (hrs.) | Viscosity | Texture |
| 1. | Test (20.4% H$_2$O) | 16 | heavy, sl. thinner than control | cohesive |
| 2. | Control (12.1% H$_2$O) | 0 | heavy | cohesive |
| 3. | Test (20.4% H$_2$O) | 4 | heavy | cohesive |
| 4. | Control (12.1% H$_2$O) | 0 | heavy | cohesive |
| 5. | Test (20.4% H$_2$O) | 7 | heavy | cohesive |
| 6. | Control (12.1% H$_2$O) | 0 | heavy | cohesive |

[a]Samples were obtained from National Starch and Chemical Company, Bridgewater, New Jersey.
[b]Process was conducted at pH 5.2.
[c]See Example 2 for cook conditions.

The results demonstrate that moisture added during the process yields a product which is as cohesive and undesirable as a control starch which had not been heated.

Part B

Samples (900 g) of a commercial granular waxy maize starch (obtained from National Starch and Chemical Company, Bridgewater, N.J.) were placed in a 10"×15"×0.75" aluminum tray and heated in an oven at 180° C. for 15, 30, 45 and 60 minutes. The pH of the starch was not adjusted and remained at about 5.2 during the heating process. Sample viscosity and texture were evaluated by the method of Example 1.

As shown below, the pH 5.2 samples were characterized by an undesirable, cohesive texture similar to that of a waxy maize starch control which had not been heat treated.

Effect of Acidic Process pH

| Sample | Process Variables[a] Heating Time (minutes) | Cold Evaluation of Gelatinized Starch[b] Viscosity | Texture |
|---|---|---|---|
| 1 | 15 | v. heavy | cohesive |
| 2 | 30 | v. heavy | cohesive |
| 3 | 45 | v. heavy | cohesive |
| 4 | 60 | heavy to v. heavy | cohesive |
| control | 0 | v. heavy | cohesive |

[a]The pH was not adjusted from that of the native waxy maize starch (a pH = 5.2) and Samples 1–4 correspond to starch treated by the process of U.S. Pat. No. 4,303,451 (no pH adjustment).
[b]See Example 2 for cook conditions.

Thus, a combination of selected factors, including the pH, moisture content and the type of native starch, determine whether a desirable, non-cohesive, heat-stable starch thickener is produced by the process of this invention.

EXAMPLE 4

This example shows carrying out the thermal inhibition in the fluidized bed previously described. The effects of temperature and time at the indicated temperature on the level of inhibition of waxy maize granular starch at pH 9.5 are shown below.

| Heating Temperature and Time | Viscosity (B.U.) Peak | Peak + 10' | Breakdown (%) |
|---|---|---|---|
| Control (none) | 1135 | 730 | 64.3 |
| 110° C. for 22 hrs. | 1185 | 970 | 18.1 |
| 160° C. for 0 hr. | 1055 | 880 | 16.6 |
| 160° C. for 2 hrs. | 665 | 660 | 0.7 |
| 175° C. for 0 hr. | 850 | 755 | 11.2 |
| 180° C. for 0 hr. | 715 | 680 | 4.9 |
| 190° C. for 0 hr. | 555 | 550 | 0.9 |
| 200° C. for 0 hr. | rising | — | — |
| 200° C. for 2 hrs. | none | — | — |

The data shows that inhibited anhydrous or substantially anhydrous samples can be obtained at heat treating temperatures between 100°–200° C., with more inhibition obtained at higher temperatures or at longer times at lower temperatures. The starch samples heated at 200° C. were highly inhibited (rising curves) or completely inhibited (no gelatinization).

EXAMPLE 5

Samples of a granular high amylose starch (Hylon V-50% amylose) at its natural pH and pH 9.5 were evaluated for the effect of the high amylose content on inhibition. The starches were thermally-inhibited at 160° C. in the fluidized bed for the indicated time. Due to the high levels of amylose, it was necessary to use a pressurized Visco/amylo/Graph (C. W. Brabender, Hackensack, N.J.) to obtain Brabender curves. Samples were slurried at 10% starch solids, heated to 120° C., and held for 30 minutes.

The results are shown below:

| High Amylose Corn | Natural pH Viscosity (BU) | | | pH 9.5 Viscosity (BU) | | |
|---|---|---|---|---|---|---|
| | Peak | Peak + 10' | Breakdown (%) | Peak | Peak + 10' | Breakdown (%) |
| Control | 1180 | 525 | 55.5 | 1180 | 525 | 55.5 |
| T-I (0 min.) | 700 | 235 | 66 | | | |
| T-I (120 min.) | 282 | 25 | 91 | 290 | 225 | 22 |

The data show that inhibition was obtained only on the high pH sample.

EXAMPLE 6

This example shows the preparation of pregelatinized granular, thermally-inhibited waxy maize starches. The pregelatinization step was carried out prior to the thermal inhibition. The fluidized bed described previously was used.

Starch slurries (30–40% solids), pH adjusted to 6, 8, and 10, were pregelatinized in a pilot size spray drier (Type-1-KA#4F, from APV Crepaco, Inc., Dryer Division, of Attleboro Falls, Mass.) using a spray nozzle, Type 1/2 J, from Spraying Systems Company of Wheaton, Ill. The spray nozzle had the following configuration: fluid cap, 251376, and air cap, 4691312.

The resulting high and low viscosity pregelatinized granular starches were dehydrated and heat treated at the temperature and time indicated. The thermally-inhibited starches were evaluated for inhibition using the Brabender procedure previously described.

The results are shown below:

| Heat Treatment Conditions | Viscosity (B.U.) | | | | | |
|---|---|---|---|---|---|---|
| | 30° C. | 30° C. + 10' | Peak | 95° C. | 95° C. + 10' | Breakdown (%) |
| pH 6.0 - High Initial Viscosity | | | | | | |
| Control | 1280 | 960 | 960 | 170 | 90 | 91 |
| 160° C. for 0 min. | 700 | 980 | 700 | 610 | 370 | 47 |
| 160° C. for 30 min. | 600 | 910 | 720 | 690 | 370 | 49 |
| 160° C. for 90 min. | 450 | 780 | 915 | 740 | 400 | 56 |
| 160° C. for 150 min. | 360 | 590 | 925 | 800 | 500 | 46 |
| pH 6.0 - | | | | | | |

-continued

| Heat Treatment Conditions | Viscosity (B.U.) | | | | | Breakdown (%) |
|---|---|---|---|---|---|---|
| | 30° C. | 30° C. + 10' | Peak | 95° C. | 95° C. + 10' | |
| Low Initial Viscosity | | | | | | |
| Control | 230 | 250 | 750 | 340 | 100 | 87 |
| 160° C. for 30 min. | 100 | 130 | 600 | 370 | 210 | 65 |
| 160° C. for 60 min. | 100 | 140 | 730 | 500 | 260 | 64 |
| 160° C. for 120 min. | 100 | 130 | 630 | 430 | 260 | 59 |
| 160° C. for 180 min. | 90 | 120 | 550 | 390 | 240 | 56 |
| pH 8.0 - | | | | | | |
| High Initial Viscosity | | | | | | |
| Control | 1400 | 1020 | 1020 | 270 | 100 | 90 |
| 160° C. for 0 min. | 700 | 1060 | 1050 | 760 | 280 | 73 |
| 160° C. for 60 min. | 260 | 600 | 1340 | 1200 | 780 | 42 |
| 160° C. for 90 min. | 240 | 440 | 1280 | 1240 | 1000 | 22 |
| 160° C. for 120 min. | 280 | 420 | 1120 | 1320 | 1280 | 3 |
| 160° C. for 150 min. | 120 | 200 | 860 | 860 | 820 | 7 |
| 160° C. for 180 min. | 180 | 260 | 980 | 980 | 920 | 8 |
| pH 8.0 - | | | | | | |
| Low Initial viscosity | | | | | | |
| Control | 250 | 250 | 820 | 340 | 130 | 84 |
| 160° C. for 0 min. | 50 | 100 | 690 | 460 | 270 | 61 |
| 160° C. for 60 min. | 40 | 50 | 840 | 590 | 320 | 62 |
| 160° C. for 120 min. | 20 | 30 | 720 | 650 | 450 | 38 |
| 160° C. for 180 min. | 20 | 30 | 590 | 570 | 450 | 24 |
| pH 10 - | | | | | | |
| High Initial Viscosity | | | | | | |
| Control | 1010 | 740 | 1010 | 300 | 160 | 84 |
| 140° C. for 0 min. | 550 | 850 | 1280 | 1080 | 750 | 41 |
| 150° C. for 0 min. | 270 | 420 | 1680 | 1680 | 1540 | 8 |
| 160° C. for 0 min. | 170 | 240 | — | 1180 | 1440 | ris. |
| 160° C. for 30 min. | 80 | 85 | — | 410 | 650 | ris. |
| 160° C. for 60 min. | 60 | 60 | — | 150 | 300 | ris. |
| 160° C. for 90 min. | 50 | 50 | — | 80 | 140 | ris. |
| 120° C. for 120 min. | 40 | 40 | — | 80 | 130 | ris. |
| 150° C. for 150 min. | 40 | 40 | — | 60 | 90 | ris. |
| 160° C. for 160 min. | 40 | 40 | — | 45 | 70 | ris. |
| pH 10 - | | | | | | |
| Low Initial Viscosity | | | | | | |
| Control | 200 | 190 | 615 | 350 | 190 | 69 |
| 130° C. for 0 min. | 110 | 180 | 1500 | 880 | 530 | 65 |
| 150° C. for 0 min. | 50 | 80 | 1670 | 1540 | 1250 | 25 |
| 160° C. for 0 min. | 30 | 30 | — | 1040 | 1320 | ris. |
| 160° C. for 30 min. | 30 | 30 | — | 380 | 640 | ris. |
| 160° C. for 60 min. | 30 | 30 | — | 150 | 310 | ris. |
| 160° C. for 90 min. | 10 | 10 | — | 50 | 120 | ris. |

The results show some thermal inhibition was attained in all the dehydrated and heat treated pregelatinized granular starches and that increasing the initial pH and the heat treatment time increased the level of inhibition. For the samples at pH 6.0, at 0 and 30 minutes, the recorded peak was actually a second peak obtained after the initial high viscosity began to breakdown. For some of the samples at pH 10, no peak viscosity was reached, indicating a highly inhibited starch.

EXAMPLE 7

This example describes the preparation of thermally-inhibited pregelatinized granular starches from additional starch bases as well as a waxy maize starch. The granular starches were adjusted to the indicated pH, pregelatinized using the procedure previously described, and heat treated in an oven at 140° C. for the indicated time. The cook evaluation and Brabender results are shown below.

| pH | Heat Treatment Hours | Viscosity of Cook | Texture of Cook |
|---|---|---|---|
| | | Cook Evaluation - Waxy Maize | |
| 6 | 2 | mod. | sl. cohesive, smooth |
| 6 | 4 | mod. | sl. cohesive, smooth |
| 6 | 6 | mod. | v. sl. cohesive, smooth |
| 6 | 8 | mod. | v. sl. cohesive, smooth |
| 8 | 2 | mod. | cohesive, smooth |
| 8 | 4 | mod. to heavy | sl. cohesive, smooth |
| 8 | 6 | moderate | v. sl. cohesive, |

| | | | |
|---|---|---|---|
| 8 | 8 | moderate | smooth v. sl. cohesive, smooth |
| 10 | 2 | mod. | sl. cohesive, smooth |
| 10 | 4 | mod. to heavy | non-cohesive, short, smooth |
| 10 | 6 | mod. | non-cohesive, short, smooth |
| 10 | 8 | mod. | non-cohesive, short, smooth |
| Cook Evaluation - Tapioca | | | |
| 6 | 2 | mod. to heavy | v. cohesive, long |
| 6 | 4 | mod. to heavy | cohesive |
| 6 | 6 | mod. | sl. cohesive, smooth |
| 6 | 8 | mod. | non-cohesive, short, smooth |
| 8 | 2 | mod. to heavy | v. cohesive |
| 8 | 4 | mod. to heavy | cohesive |
| 8 | 6 | mod. to heavy | non-cohesive, short, smooth |
| 8 | 8 | mod. to heavy | non-cohesive, short, smooth |
| 10 | 2 | mod. to heavy | cohesive, long |
| 10 | 4 | mod. to heavy | v. sl. cohesive, smooth |
| 10 | 6 | mod. | non-cohesive, short, smooth |
| 10 | 8 | mod. to heavy | non-cohesive, short, smooth |
| Cook Evaluation - Potato | | | |
| 6 | 2 | heavy to v. heavy | v. cohesive, long |
| 6 | 4 | heavy | cohesive |
| 6 | 6 | mod. to heavy | sl. cohesive |
| 6 | 8 | mod. to heavy | v. sl. cohesive |
| 8 | 2 | heavy to v. heavy | v. cohesive, long |
| 8 | 4 | v. heavy | sl. cohesive |
| 8 | 6 | heavy | non-cohesive, sl. set, smooth |
| 8 | 8 | mod. | non-cohesive, v. sl. set, smooth |
| 10 | 2 | heavy | v. cohesive |
| 10 | 4 | heavy to mod. | sl. cohesive, sl. set, smooth |
| 10 | 6 | heavy to mod. | non-cohesive, short, mod. set, smooth |
| 10 | 8 | heavy to mod. | non-cohesive, short, mod. set, smooth |

| Heat Treatment Conditions | Viscosity (BU) | | | | | Breakdown (%) |
|---|---|---|---|---|---|---|
| | 30° C. | 30° C. + 10' | Peak | 95° C. | 95° C. + 10' | |
| Brabender Results - Waxy Maize at pH 8 and 146° C. | | | | | | |
| 2 hrs | 400 | 1115 | 1115 | 515 | 515 | 60 |
| 6 hrs | 400 | 955 | 1120 | 1120 | 1023 | 38 |
| Brabender Results - Tapioca at pH 8 | | | | | | |
| 2 hrs | 1140 | 2685 | 2685 | 2685 | 880 | 78 |
| 6 hrs | 370 | 800 | 1110 | 1110 | 890 | 46 |

The results show that thermally-inhibited pregelatinized granular starches can be prepared using other starch bases and that for non-cohesive starches longer times and/or higher pHs are required when an oven rather than a fluidized bed is used for the dehydration and heat treatment.

EXAMPLE 8

This example shows the preparation of pregelatinized, non-granular, starches which were pregelatinized by drum-drying and then thermally inhibited.

Samples of waxy maize, tapioca and potato starches, at pH 6, 8, and 10, were pregelatinized by drum-drying. The samples were placed in a 140° C. oven, dehydrated to anhydrous, and heat treated at 140° C. for the indicated times.

The viscosity and textural characteristics of the thermally-inhibited starches are set out below.

| Time | Cook Viscosity | Cook Texture |
|---|---|---|
| T-I Waxy Maize - pH 6 | | |
| 2 hrs | heavy | v. cohesive, pulpy |
| 4 hrs | heavy to v. heavy | cohesive, pulpy |
| 6 hrs | heavy | sl. cohesive, pulpy |
| 8 hrs | mod. to heavy | v. sl. cohesive, pulpy |
| T-I Waxy Maize - pH 8 | | |
| 2 hrs | heavy | v. cohesive, pulpy |
| 4 hrs | heavy | sl. cohesive, pulpy |
| 6 hrs | mod. to heavy | v. sl. cohesive, pulpy |
| 8 hrs | mod. to heavy | v. sl. cohesive, pulpy |
| T-I Navy Maize - pH 10 | | |
| 2 hrs | heavy | cohesive, pulpy |
| 4 hrs | heavy to mod. | v. si. cohesive, pulpy |
| 6 hrs | mod. | non-cohesive, short, pulpy |
| 8 hrs | mod. | non-cohesive, short, pulpy |
| T-I Tapioca - pH 6 | | |
| 2 hrs | v. heavy | cohesive, pulpy |
| 4 hrs | heavy to v. heavy | sl. cohesive, pulpy |
| 6 hrs | mod. heavy | sl. cohesive, pulpy |
| 8 hrs | heavy | sl. cohesive, pulpy |
| T-I Tapioca - pH 8 | | |
| 2 hrs | heavy to v. heavy | v. cohesive, pulpy |
| 4 hrs | heavy | v. cohesive, pulpy |
| 6 hrs | N.D. | N.D. |
| 8 hrs | heavy | v. sl. cohesive, pulpy |
| T-I Tapioca 10 - pH | | |
| 2 hrs | heavy | cohesive, pulpy |
| 4 hrs | heavy to v. heavy | sl. cohesive, pulpy |
| 6 hrs | heavy | non-cohesive, short, pulpy |
| 8 hrs | mod. heavy | non-cohesive, short, pulpy |
| T-I Potato - pH 6 | | |
| 2 hrs | heavy to v. heavy | cohesive, pulpy |
| 4 hrs | heavy | cohesive, pulpy |
| 6 hrs | mod. to heavy | cohesive, pulpy |
| 8 hrs | mod. to heavy | cohesive, pulpy |
| T-I Potato - pH 8 | | |
| 2 hrs | heavy to v. heavy | v. cohesive, pulpy |
| 4 hrs | v. heavy | cohesive, pulpy |
| 6 hrs | v. heavy | cohesive, pulpy |
| 8 hrs | v. heavy | cohesive, pulpy |
| T-I Potato - pH 10 | | |
| 2 hrs | heavy to v. heavy | v. cohesive, pulpy |
| 4 hrs | v. heavy | slight set, sl. chunky |
| 6 hrs | heavy | slight set, sl. chunky |
| 8 hrs | mod. heavy | moderate set, sl. chunky |

Brabenders were run on some of the above starches. The results are shown below.

| | Viscosity (BU) | | | | | |
|---|---|---|---|---|---|---|
| | 30° C. | 30° C. + 10' | Peak | 95° C. | 95° C. + 10' | Break-down (%) |
| T-I Waxy Maize - pH 8 | | | | | | |
| 2 hrs. | 665 | 3000 | 4620 | 1120 | 300 | 94 |
| 6 hrs. | 700 | 1640 | 2445 | 2440 | 1900 | 22 |
| T-I Tapioca - pH 8 | | | | | | |
| 2 hrs. | 1500 | 3170 | 3290 | 680 | 600 | 82 |
| 6 hrs. | 1180 | 1870 | 1873 | 780 | 600 | 68 |

The results show that longer heating times and/or higher pHs are required to prepare non-cohesive starches at 140° C. It is expected that heating at 160° C., preferably in a fluidized bed, will provide non-cohesive starches.

EXAMPLE 9

This example shows the preparation of another pregelatinized non-granular starch which was jet-cooked, spray-dried, and then thermally inhibited.

A granular high amylose starch (50% amylose) was jet-cooked and spray-dried using the continuous coupled jet-cooking/spray-drying process described in U.S. Pat. No. 5,131,953 and then thermally inhibited for 8 hours at 140° C. The jet-cooking/spray-drying conditions used were as follows: slurry—pH 8.5–9.0; cook solids—10%; moyno setting—about 1.5; cooking temperature—about 145° C.; excess steam—20%; boiler pressure—about 85 psi; back pressure—65 psi; spray-dryer—Niro dryer; inlet temperature—245° C.; outlet temperature—115° C.; atomizer—centrifugal wheel. The pregelatinized non-granular starch was adjusted to pH 8.7 and dehydrated and heat treated for 8 hours in an oven at 140° C. The characteristics of the resulting thermally-inhibited starches are set out below.

| High Amylose - pH 8.7 | | | | | | |
|---|---|---|---|---|---|---|
| | Viscosity (BU) | | | | | |
| | 30° C. | 30° C. + 10' | Peak | 95° C. | 95° C. + 10' | Break-down (%) |
| Control | 200 | 195 | 245 | 245 | 130 | 47 |
| T-I Starch | 350 | 240 | 420 | 410 | 335 | 20 |

The results show that even a high amylose starch can be inhibited. There was less breakdown for the thermally-inhibited starch and the overall viscosity was higher.

EXAMPLE 10

The example shows that thermally-inhibited waxy maize starches can be prepared by drum drying the starches prior to thermal inhibition. The resulting non-granular thermally-inhibited drum-dried starches are compared with the non-granular thermally-inhibited waxy maize starches prepared by the continuous coupled jet-cooking and spray-drying process used in Example 9 and with granular thermally-inhibited starches prepared by the dual atomization/spray drying process described in U.S. Pat. No. 4,280,251 (which was used in Example 6). The conditions used for the oven dehydration and heat treatment were 8 hours at 140° C.

The characterization of the resulting thermally-inhibited pregelatinized starches is shown below.

| | Viscosity (BU) | | | | | |
|---|---|---|---|---|---|---|
| | 30° C. | 30° C. + 10' | Peak | 95° C. | 95° C. + 10' | Break-down (%) |
| Drum-Dried/Non-Granular T-I - pH 8 Waxy Maize | | | | | | |
| Control | 640 | 2770 | 3,530 | 1,690 | 1,550 | 56 |
| T-I Starch | 700 | 1640 | 2,440 | 2,365 | 1,860 | 24 |
| Jet-Cooked/Spray-Dried/Non-Granular T-I Waxy Maize - pH 8 | | | | | | |
| Control | 60 | 90 | 100 | 41 | 30 | 70 |
| T-I Starch | 485 | 1540 | 1,545 | 1,330 | 1,230 | 20 |
| Steam Atomized/Spray-Dried/Granular T-I Waxy Maize - pH 8 | | | | | | |
| Control | 100 | 1010 | 1,080 | 340 | 170 | 84 |
| T-I Starch | 360 | 950 | 970 | 860 | 650 | 33 |

The results show that after 8 hours heat treatment at 140° C. all the pregelatinized thermally-inhibited starches showed much less breakdown. The results also show that a higher degree of inhibition along with a higher peak viscosity can be obtained if the starch granules are completely disrupted as by drum drying or jet cooking.

EXAMPLE 11

Waxy maize, tapioca, and potato starches were adjusted to pH 8 and drum dried (DD) before and after being thermally inhibited (T-I) by dehydrating and heat treating at 140° C. for 8 hours.

The Brabender results are shown below.

| | | Viscosity (BU) | | | | | |
|---|---|---|---|---|---|---|---|
| Conditions | | 30° C. | 30° C. + 10' | Peak | 95° C. | 95° C. +10' | Break-down |
| Waxy Maize - pH 8 | | | | | | | |
| Control | — | 640 | 2770 | 3530 | 380 | 122 | 97% |
| T-I Starch | DD/TI — | 642 | 1080 | 1700 | 1670 | 1510 | 11% |

-continued

| Conditions | | | Viscosity (BU) | | | | | |
|---|---|---|---|---|---|---|---|---|
| | | | 30° C. | 30° C. + 10' | Peak | 95° C. | 95° C. +10' | Breakdown |
| T-I Starch Tapioca - pH 8 | — | TI/DD | 650 | 2040 | 2850 | 840 | 480 | 83% |
| Control | — | — | 500 | 2600 | 2800 | 185 | 45 | 98% |
| T-I Starch | DD/TI | — | 720 | 1165 | 1170 | 730 | 570 | 51% |
| T-I Starch Potato - pH 8 | — | TI/DD | 590 | 1345 | 1365 | 530 | 370 | 73% |
| Control | — | — | 170 | 1355 | 1395 | 185 | 75 | 95% |
| T-I Starch | DD/TI | — | 380 | 935 | 1035 | 965 | 740 | 29% |
| T-I | — | TI/DD | 390 | 990 | 1010 | 610 | 450 | 55% |

DD/TI indicates that the drum drying was carried out before the thermal inhibition (dehydrating and heat treating at 140° C. for 8 hrs).

TI/DD indicates that the thermal inhibition (dehydrating and heat treating at 140° C. for 8 hrs) was carried out before the drum drying.

The results show that thermally-inhibited, starches can be prepared when the drum drying is carried out after the thermal inhibition.

EXAMPLE 12

This example shows that a granular starch can be dehydrated by ethanol (EtOH) extraction and that a better tasting starch is obtained.

A granular waxy maize starch was slurried in 1.5 parts water based on the weight of the starch and adjusted to pH 7 and 9.5 with 5% sodium carbonate, held for 30 minutes, filtered, and dried on a tray to a moisture content of about 5–6% moisture. The starch having the pH of 5.3 was a native starch which was not pH adjusted.

For the dehydration, the dried pH 5.3, pH 7.0, and pH 9.5 starches were each separated into two samples. One sample was dried on trays in a forced draft oven at 80° C. overnight to thermally dehydrate the starch to <1% (0%) moisture. The other sample was placed in a Soxhlet extractor and allowed to reflux overnight (about 17 hours) with anhydrous ethanol (boiling point 78.32° C.). The ethanol-extracted sample was placed on paper so that the excess alcohol could flash off which took about 30 minutes. The ethanol-extracted starch was a free flowing powder which was dry to the touch.

For the heat treatment, the oven-dehydrated starches and ethanol-extracted starches were placed on trays in a forced draft oven and heated for 3, 5, and 7 hours at 160° C.

The thermally-inhibited (T-I) starches and the controls were evaluated using the Brabender Procedure previously described was used. The results are shown below:

| | | | BRABENDER RESULTS | | |
|---|---|---|---|---|---|
| | | | | Viscosity (BU) | |
| Waxy Maize (pH 5.3) | Dehydration Method | Heat Treatment (160° C.) | Peak | Peak + 10' | Breakdown (%) |
| Control | — | — | 1245 | 330 | 74 |
| Dehydrated | oven | — | 1290 | 350 | 73 |
| Dehydrated | ethanol | — | 1205 | 245 | 80 |
| T-I | oven | 5 hrs. | 95 | 45 | 53 |
| T-I | ethanol | 5 hrs. | 255 | 185 | 28 |
| T-I | oven | 7 hrs. | 60 | 35 | 42 |
| T-I | ethanol | 7 hrs. | 165 | 105 | 36 |
| Waxy Maize (pH 7.0) | | | | | |
| Dehydrated | oven | — | 1240 | 380 | 69 |
| T-I | oven | 7 hrs. | 298 | 240 | 20 |
| T-I | ethanol | 7 hrs. | 400 | 310 | 23 |
| Waxy Maize (pH 9.5) | | | | | |
| Dehydrated | oven | — | 1250 | 400 | 68 |
| Dehydrated | ethanol | — | 1070 | 350 | 67 |
| T-I | ethanol | 3 hrs. | 665 | 635 | 5 |
| T-I | oven | 3 hrs. | 680 | 655 | 4 |
| T-I | oven | 5 hrs. | 245 | 460 | ris. |
| T-I | ethanol | 5 hrs. | 160 | 375 | ris. |
| T-I | oven | 7 hrs. | 110 | 295 | ris. |
| T-I | ethanol | 7 hrs. | 110 | 299 | ris. |

The results show that the starches can be dehydrated by ethanol extraction. The results also show that dehydration without the subsequent heat treatment did not inhibit the starch. The viscosity breakdown was not significantly different from that of the native waxy maize starch. Both of the thermally-inhibited pH 7 starches were higher in viscosity than the pH 5.3 (as is) thermally-inhibited starches. The starches which were thermally-inhibited at pH 9.5 were moderately highly inhibited or highly inhibited (rising curve).

EXAMPLE 13

Granular tapioca, corn, and waxy rice starches and waxy rice flour were adjusted to pH 9.5, dehydrated in an oven and by extraction with ethanol, and heat treated at 160° C. for the indicated time. They were evaluated for Brabender viscosity using the procedure previously described.

The Brabender results are shown below.

| Starch Base | Dehydration Method | Heat Treatment Time | Viscosity (BU) Peak | Peak + 10' | Breakdown % |
|---|---|---|---|---|---|
| Tapioca | | | | | |
| Dehydrated | oven | — | 745 | 330 | 58 |
| Dehydrated | ethanol | — | 720 | 330 | 54 |
| T-I | oven | 5 hrs. | 270 | 260 | 3 |
| T-I | ethanol | 5 hrs. | 260 | 258 | 1 |
| T-I | oven | 7 hrs. | 110 | 155 | ris. |
| T-I | ethanol | 7 hrs. | 100 | 145 | ris. |
| Corn | | | | | |
| Dehydrated | oven | — | 330 | 280 | 15 |
| Dehydrated | ethanol | — | 290 | 250 | 14 |
| T-I | oven | 5 hrs. | 10 | 80 | ris. |
| T-I | ethanol | 5 hrs. | 10 | 170 | ris. |
| T-I | oven | 7 hrs. | 10 | 65 | ris. |
| T-I | ethanol | 7 hrs. | 10 | 45 | ris. |
| Waxy Rice | | | | | |
| Dehydrated | oven | — | 1200 | 590 | 50.8 |
| Dehydrated | ethanol | — | 1155 | 450 | 61.0 |
| T-I | oven | 5 hrs. | 518 | 640 | ris. |
| T-I | oven | 7 hrs. | 265 | 458 | ris. |
| T-I | ethanol | 7 hrs. | 395 | 520 | ris. |
| Waxy Rice Flour | | | | | |
| Dehydrated | oven | — | 895 | 700 | 22 |
| Dehydrated | ethanol | — | 870 | 410 | 53 |
| T-I | oven | 5 hrs. | 38 | 73 | ris. |
| T-I | ethanol | 5 hrs. | 140 | 260 | ris. |
| T-I | oven | 7 hrs. | 10 | 16 | ris. |
| T-I | ethanol | 7 hrs. | 40 | 100 | ris. |

The results show that pH 9.5-adjusted, ethanol-extracted, heat-treated tapioca and corn starches had viscosity profiles generally similar to those of the same thermally-inhibited starches which were oven-dehydrated. The 7 hours heat-treated samples were more inhibited than the 5 hour heat-treated samples.

EXAMPLE 14

This example compares ethanol extracted granular waxy maize starches and oven-dehydrated granular waxy maize starches heat treated in an oven for 5 and 7 hours at 160° C. at the same pH, i.e., pH 8.03.

The Brabender results are shown below.

| Dehydration/ Heat Treatment | Viscosity (BU) Peak | Peak + 10' | Breakdown (%) |
|---|---|---|---|
| Oven/None | 1160 | 360 | 69 |
| EtOH/None | 1120 | 370 | 67 |
| Oven/5 hrs. | 510 | 455 | 11 |
| EtOH/5 hrs. | 490 | 445 | 9 |
| Oven/7 hrs. | 430 | 395 | 8 |
| EtOH/7 hrs. | 360 | 330 | 8 |

The thermally-inhibited starches were slurried at 6.6% solids (anhydrous basis), pH adjusted to 6.0–6.5, and then cooked out in a boiling water bath for 20 minutes. The resulting cooks were allowed to cool and then evaluated for viscosity, texture, and color.

| Dehydration Method | Time at 160° C. | Viscosity | Texture | Color |
|---|---|---|---|---|
| Oven | None | heavy to v. heavy | cohesive | sl. off-white |
| Ethanol | None | heavy to v. heavy | cohesive | sl. off-white |
| Oven | 5 hours | mod. heavy to heavy | non-cohesive, smooth | sl. tan, darker* |
| Ethanol | 5 hours | mod. heavy to heavy | non-cohesive, smooth | sl. tan |
| Oven | 7 hours | mod. heavy to heavy | non-cohesive, smooth | mod. tan, darker* |
| Ethanol | 7 hours | mod. heavy to heavy | non-cohesive, smooth | mod. tan |

*Slightly darker than ethanol-dehydrated samples.

These Brabender results show that highly inhibited starches can be obtained by both thermal and non-thermal dehydration. The cook evaluation results show that there is a benefit for the ethanol-dehydrated, thermally-inhibited starches in terms of reduced color. As will be shown hereafter, there is also a flavor improvement with ethanol dehydration.

EXAMPLE 15

A granular waxy maize starch was pH adjusted to pH 9.5 as previously described. The starch was then placed in a freeze dryer and dried for 3 days until it was anhydrous (0% moisture). The freeze-dried (FD) starch was heat treated for 6 and 8 hours at 160° C. in a forced draft oven.

Brabender evaluations were run. The results are shown below:

| Base | Heat Treatment (160° C.) | Viscosity (BU) Peak | Peak + 10' | Breakdown (%) |
|---|---|---|---|---|
| Control | — | 1260 | 320 | 75 |
| F.D. | — | 1240 | 320 | 74 |
| T-I | 6 hrs. | 340 | 465 | ris. |
| T-I | 8 hrs. | 285 | 325 | ris. |

The results show that the starch can be dehydrated by freeze drying and that the subsequent heat treatment is necessary to inhibit the starch. The starches are highly inhibited as shown by their rising viscosity.

EXAMPLE 16

This example shows that thermal inhibition reduced the gelatinization temperature of the granular waxy maize starches.

The gelatinization temperature of an untreated waxy maize, a thermally-inhibited (T-I) waxy maize (pH adjusted and not pH adjusted), and chemically-crosslinked (X-linked) waxy maize starches (0.02%, 0.04%, and 0.06% phosphorus oxychloride) were determined by Differential Scanning Calorimetry. The starches were thermally dehydrated and heat treated in an oven for the indicated time and temperature.

The peak gelatinization temperature and enthalpy (ΔH) are shown below.

| Waxy Maize | Gelatinization Temperature (°C.) | Enthalpy (Δ H) (cal/g) |
|---|---|---|
| Unmodified | 74 | 4.3 |
| T-I (pH 9.5;160° C. for 8.5 hrs.) | 68 | 2.9 |
| T-I Waxy Maize (pH 6;160° C. for 8 hrs.) | 59 | 2.8 |
| X-linked (0.02% POCl₃) | 73 | 4.4 |
| X-linked (0.04% POCl₃) | 72 | 4.2 |
| X-linked (0.06% POCl₃) | 74 | 4.2 |

The results show that there was a significant reduction in peak gelatinization temperature of the thermally inhibited (T-I) starches. The chemically crosslinked (X-linked) starches are essentially identical to the unmodified waxy starch in peak gelatinization temperature (72°–74° C. vs. 74° C.) and enthalpy (4.2–4.4 vs 4.3 cal/g). The reduced gelatinization temperature suggests that the overall granular structure has been altered by the dehydration and heat treatment.

EXAMPLE 17

This example shows that the thermal inhibition may begin as early as 110° C. (230° F.), that it is substantially noticeable at 160° C. (320° F.), and that the gelatinization is unchanged or reduced. Granular waxy maize starches were pH adjusted to 7.0 and 9.5 and dehydrated and heat treated using air having a Dew point below 9.4° C. (15° F.) in the fluidized bed previously described at the indicated temperature and time.

The Brabender and DSC results are shown below.

| Waxy Maize (pH 7.0) | | | |
|---|---|---|---|
| Dehydration/ | Brabender Viscosity (BU) | | |
| Heat Treatment Conditions | Peak | Peak + 10' | Breakdown (%) |
| Control* | 1010 | 220 | 78.2 |
| 93° C. for 0 min. | 1010 | 220 | 78.2 |
| 116° C. for 0 min.. | 1030 | 250 | 75.7 |
| 127° C. for 0 min. | 1050 | 260 | 75.2 |
| 149° C. for 0 min. | 1130 | 350 | 69.0 |
| 160° C. for 0 min. | 1010 | 590 | 41.6 |
| 160° C. for 10 min. | 980 | 630 | 35.7 |
| 160° C. for 20 min. | 910 | 610 | 33.0 |
| 160° C. for 80 min. | 750 | 510 | 32.0 |
| 160° C. for 90 min. | 735 | 510 | 30.6 |

| *Not pH-adjusted. | | |
|---|---|---|
| Dehydration/ Heat Treatment Conditions | Peak Gelatinization Temperature** | Enthalpy** (cal/g) |
| Control* | 73.07 | 4.43 |
| 93° C. for 0 min. | 71.79 | 4.01 |
| 116° C. for 0 min. | 70.70 | 4.18 |
| 127° C. for 0 min. | 70.66 | 4.07 |
| 149° C. for 0 min. | 70.07 | 3.92 |
| 160° C. for 0 min. | 69.50 | 4.08 |
| 160° C. for 10 min. | 71.20 | 4.17 |
| 160° C. for 20 min. | 68.87 | 4.32 |
| 160° C. for 80 min. | 67.84 | 4.35 |
| 160° C. for 90 min. | 67.29 | 4.38 |

*Not pH-adjusted.
**Average of 2 readings.

| Waxy Maize (pH 9.5) | | | |
|---|---|---|---|
| Dehydration/ | Brabender Viscosity (BU) | | |
| Heat Treatment Conditions | Peak | Peak + 10' | Breakdown (%) |
| Control (pH 9.5) | 1240 | 300 | 75.8 |
| 93° C. for 0 min. | 1200 | 300 | 75.0 |
| 104° C. for 0 min. | 1205 | 320 | 73.4 |
| 110° C. for 0 min. | 1260 | 400 | 68.3 |
| 121° C. for 0 min. | 1230 | 430 | 65.0 |
| 127° C. for 0 min. | 1255 | 420 | 66.5 |
| 138° C. for 0 min. | 1245 | 465 | 62.7 |
| 149° C. for 0 min. | 1300 | 490 | 62.3 |
| 160° C. for 0 min. | 1120 | 910 | 18.8 |
| 160° C. for 60 min. | 750 | 730 | 2.7 |
| 160° C. for 90 min. | 690 | 680 | 1.4 |

| Dehydration/ Heat Treatment Conditions | Gelatinization Peak Temperature* (°C.) | Enthalpy* (cal/g) |
|---|---|---|
| Control (pH 9.5) | 74.82 | 4.05 |
| 127° C. for 0 min. | 74.84 | 4.17 |
| 160° C. for 0 min. | 73.04 | 4.50 |
| 160° C. for 60 min. | 71.84 | 4.60 |
| 160° C. for 90 min. | 70.86 | 4.26 |

*Average of 2 readings.

The DSC results show that at the onset of inhibition there was a slight reduction in the peak gelatinization temperature and that as the inhibition temperature and time increased there was a reduction in peak gelatinization temperature.

EXAMPLE 18

This example shows the correlation between the RVA pasting temperature and time and DSC peak gelatinization temperature and time and the reduction in Brabender viscosity breakdown for various granular starch bases and for granular waxy maize starches dehydrated by various methods including heating, ethanol extraction, and freeze drying. The base starches were unmodified. The starches were all adjusted to pH 9.5 before dehydration. The ethanol-extracted and freeze-dried controls were pH adjusted and dehydrated but not heat treated. The dehydrated starches were all heat treated in an oven at 160° C. for the indicated time except for the starches chemically crosslinked with sodium trimetaphosphate (STMP) which were heat treated at 160° C. for the indicated time in the fluidized bed previously described.

The results are shown below.

| Starch | Pasting Temp. (°C.) | Pasting Time (min) | DSC Peak Temp. (°C.) | DSC Peak Time (min) | Viscosity (B.U.) Peak | Viscosity (B.U.) Peak + 10' | Breakdown (%) |
|---|---|---|---|---|---|---|---|
| Tapioca Dehydrated/Thermally/Heat Treated at 160° C. | 68.20 | 3.7 | 70.61 | 6.6 | 1595 | 440 | 72.41 |
| T-I (2 hrs.) | 66.65 | 3.4 | 68.31 | 6.3 | 1230 | 560 | 54.47 |
| T-I (6 hrs.) | 64.20 | 2.9 | 65.41 | 6.0 | 355 | 335 | 5.63 |
| Potato Dehydrated/Heat Treated at 160° C. | 61.05 | 2.3 | 62.67 | 5.8 | 1825 | 1010 | 44.66 |
| T-I (3 hrs.) | 60.25 | 2.1 | 61.41 | 5.6 | 995 | 810 | 18.59 |
| T-I (6 hrs.) | 60.20 | 2.1 | 61.13 | 5.6 | ris. | ris. | ris. |
| Waxy Maize Thermally Dehydrated/Thermally/Heat Treated at 160° C. | 70.95 | 4.3 | 73.86 | 6.9 | 1215 | 350 | 71.79 |
| T-I (8 hrs.) | 68.15 | 3.7 | 70.71 | 6.6 | 760 | 720 | 5.26 |
| Waxy Maize Ethanol Dehydrated/Heat Treated at 160° C. | 70.95 | 4.3 | 74.23 | 6.9 | 1250 | 400 | 68.00 |
| T-I (2 hrs.) | 65.00 | 3.1 | 71.81 | 6.7 | ris. | ris. | ris. |
| T-I (7 hrs.) | 63.85 | 2.8 | 68.12 | 6.3 | ris. | ris. | ris. |
| Waxy Maize Dehydrated by Freeze Drying/Heat Treated at 160° C. | 71.30 | 4.4 | 74.16 | 6.9 | 1240 | 320 | 74.19 |
| T-I (6 hrs.) | 69.50 | 4.0 | 66.09 | 6.1 | ris. | ris. | ris. |
| T-I (8 hrs.) | 66.75 | 3.5 | 64.64 | 6.0 | ris. | ris. | ris. |
| Cross-linked Waxy Maize Thermally Dehydrated Crosslinked Waxy Maize | 71.70 | N.D. | 74.33 | 6.9 | ris. | ris. | ris. |
| Cross-linked T-I (30 min.) | 69.10 | N.D. | 71.66 | 6.7 | ris. | ris. | ris. |
| Cross-linked T-I (150 min.) | 66.00 | N.D. | 67.14 | 6.2 | ris. | ris. | ris. |

*Fluidized bed.

The results show that heat treatment of thermally and non-thermally dehydrated granular starches reduced the pasting and peak gelatinization temperatures while at the same time inhibiting the viscosity breakdown. Because the gelatinization temperature has been lowered by the heat treatment of the dehydrated starch, less time is required to reach the pasting and gelatinization temperatures. The more highly inhibited starches showed a lower pasting temperature and less breakdown in viscosity.

EXAMPLE 19

This example describes a visual evaluation of the dry powder flow properties of granular waxy maize starches adjusted to pH 9.5 and thermally dehydrated and heat treated in the fluidized bed previously described.

The starches evaluated are shown below:

| No. | Heat Treatment Conditions |
|---|---|
| 1 | 160° C. for 30 min. |
| 2 | 160° C. for 60 min. |
| 3 | 160° C. for 180 min. |

Powder No. 1 distributed fairly evenly and the flow pattern was uniform. It was somewhat fluid and had some dynamic quality. Only a slight amount of air was entrapped in the body of the powder. Powder No. 2 distributed evenly and the flow pattern was uniform. The powder was fluid and had a dynamic quality. There was no air entrapment in the body of the powder. Powder No. 3 distributed evenly and the flow pattern was uniform. The powder was fluid, water-like, and had a dynamic quality. No air was entrapped in the body of the powder. The control starch powder clumped and had an irregular flow. It had a cake-like static quality. Air was entrapped in the body of the powder.

EXAMPLE 20

This example measures the flow properties of thermally-inhibited granular waxy maize starches by determining the angle of repose. The angle of repose is an indication of performance with regard to mobility/flow.

The starches evaluated are shown below:

| Starch Base | pH | Temperature (°C.) | Time at Final Temperature (min.) | Angle of Repose* |
|---|---|---|---|---|
| Waxy Maize | 9.5 | 160 | 30 | 24.17 |
| Waxy Maize | 9.5 | 160 | 60 | 26.75 |
| Waxy Maize | 9.5 | 160 | 180 | 23.60 |

*Average of 5 readings.

The control did not flow. The thermally-inhibited starches had good flow properties.

The angle of repose of native corn starch and chemically crosslinked and derivatized waxy corn starch could not be measured because the funnels were completely blocked upon addition of the sample. These starches would not even flow through powder funnels with larger I.D. orifices without constant tapping.

EXAMPLE 21

This example shows that the thermally-inhibited granular starches and flours are essentially sterilized by the heat-treatment and remain sterile when properly stored.

Part A—Thermally-Inhibited Waxy Rice Flour

The flour was adjusted to pH 9.5 and thermally-inhibited in the fluidized bed as previously described and stored for about 3 months in a non-sterilized, covered glass container. The thermally-inhibited flours and the control flour were microbiologically tested for their total plate count (Colony Forming Units—CFU) using the procedure described on pages 17–19 of Chapter 3 "Aerobic Plate Count" by J. T. Peeler and L. J. Maturin, FDA Bacteriological Analytical Manual, 7th Ed. (A.O.A.C. International, Arlington, Va. 1992). The results are shown below:

| | Plate Count (CFU) |
|---|---|
| None | 7500 |
| 160° for 0 min | <10 |
| 160° for 60 min | <10 |
| 160° for 120 min | <10 |

Part B—Thermally-Inhibited Waxy Maize Starch

The starch was adjusted to pH 9.5 and thermally-inhibited in the fluidized bed as previously described and stored for about 2 months in non-sterilized, covered glass containers. The thermally-inhibited starches and the control starch were microbiologically tested for their total plate count using the above procedure. The results are shown below.

| | Plate Count (CFU) |
|---|---|
| None | 2000 |
| 160° for 0 min | <10 |
| 160° for 60 min | <10 |
| 160° for 120 min | <10 |

The above results are particularly surprising, especially since the thermally-inhibited flours and starches were not handled using aseptic techniques. If stored and maintained under sterile conditions, these starches should be useful in products where microbiological considerations are of concern.

EXAMPLE 22

Waxy maize starches reacted with 7% and 3% by weight propylene oxide and thermally inhibited, at the naturally occurring pH and at pH 9.5, were evaluated for inhibition. The results set out below.

| Temp (°C.) | Time (min) | Viscosity (BU) Peak | Peak + 10' | 92° C. | 92° C. + 30' | Breakdown (%) |
|---|---|---|---|---|---|---|
| Waxy Maize (7% PO and natural pH at 160° C.) ||||||| 
| Control | | 1420 | 395 | — | — | 72 |
| 160 | 0 | 1030 | 380 | — | — | 63 |
| 160 | 30 | 800 | 530 | — | — | 34 |
| 160 | 60 | 685 | 430 | — | — | 37 |
| 160 | 90 | 635 | 340 | — | — | 46 |
| 160 | 120 | 620 | 340 | — | — | 45 |
| 160 | 150 | 565 | 300 | — | — | 47 |
| 160 | 180 | 540 | 280 | — | — | 48 |
| Waxy Maize (7% PO and natural pH at 160° C.) |||||||
| Control | | 1420 | 395 | — | — | 72 |
| 160 | 0 | 1360 | 960 | — | — | 29 |
| 160 | 30 | 1010 | 950 | — | — | 6 |
| 160 | 60 | 1030 | 930 | — | — | 10 |
| 160 | 90 | 910 | 890 | — | — | 2 |
| 160 | 120 | 843 | 830 | — | — | 2 |
| 160 | 180 | 800 | 792 | — | — | 1 |
| Waxy Maize (3% PO and natural pH) |||||||
| Control | | 1155 | 280 | — | — | 76 |
| 160 | 0 | 900 | 360 | — | — | 60 |
| 160 | 30 | 570 | 370 | — | — | 35 |
| 160 | 60 | 480 | 350 | — | — | 27 |
| 160 | 90 | 440 | 300 | — | — | 32 |
| 160 | 120 | 375 | 235 | — | — | 37 |
| 160 | 150 | 310 | 185 | — | — | 40 |
| 160 | 180 | 300 | 180 | — | — | 40 |
| Waxy Maize (3% PO and pH 9.5) |||||||
| Control | | 1155 | 280 | — | — | 76 |
| 160 | 0 | 1220 | 960 | — | — | 21 |
| 160 | 30 | 1020 | 950 | — | — | 7 |
| 160 | 60 | 880 | 865 | — | — | 2 |
| 160 | 90 | — | — | 750 | 790 | ris. |
| 160 | 120 | — | — | 620 | 780 | ris. |
| 160 | 150 | — | — | 510 | 750 | ris. |
| 160 | 180 | — | — | 400 | 700 | ris. |

The data show that derivatized starches, in this case etherified starches, can be thermally inhibited by this process and that a higher inhibition can be achieved at higher pH.

EXAMPLE 23

Waxy maize starches were reacted with 1% by weight acetic anhydride ($AC_2O$) and thermally inhibited at the naturally occurring pH and at pH 8.5.

The results are shown below.

| Temp (°C.) | Time (min) | Viscosity (BU) Peak | Peak + 10' | 92° C. | 92° C. + 30' | Breakdown (%) |
|---|---|---|---|---|---|---|
| Waxy Maize (1% acetic anhydride and natural pH at 160° C.) |||||||
| Control | | 1480 | 490 | — | — | 67 |
| 160 | 0 | 1030 | 570 | — | — | 45 |
| 160 | 30 | 880 | 650 | — | — | 26 |
| 160 | 60 | 720 | 510 | — | — | 29 |
| 160 | 120 | 605 | 490 | — | — | 19 |
| 160 | 180 | 545 | 460 | — | — | 16 |
| Waxy Maize (1% acetic anhydride and pH 8.5 at 160° C.) |||||||
| Control | | 1480 | 490 | — | — | 67 |
| 160 | 0 | 1170 | 560 | — | — | 52 |
| 160 | 30 | 970 | 725 | — | — | 25 |
| 160 | 60 | 875 | 600 | — | — | 31 |
| 160 | 120 | 690 | 490 | — | — | 29 |
| 160 | 180 | 585 | 545 | — | — | 7 |

The data show that derivatized starches, in this case esterified starches, can be inhibited to varying degrees and that higher inhibition can be obtained at higher pH.

EXAMPLE 24

A converted hydroxypropylated waxy maize (25 WF starch reacted with 2% propylene oxide) was adjusted to pH 9.5 and thermally inhibited using the fluidized bed previously described. Samples were taken at 110° C., 125° C., and 140° C., all for 0 minutes.

The thermally-inhibited starch samples were cooked in tap water at 88°–93° C. (190°–200° F.) bath temperature for 30–60 minutes to yield solutions having a Brookfield viscosity of approximately 3000 cps. The viscosity stability at room temperature was evaluated.

The results are shown below:

|  | Control* | 110° C. | 125° C. | 140° C. |
|---|---|---|---|---|
| Water Fluidity | 25.0 | 25.5 | 20.6 | 21.8 |
| Solids (%) | 18 | 18 | 18 | 18 |
| Initial Viscosity (cps) | 3160 | 2550 | 2820 | 2800 |
| Viscosity after 24 hours (cps) | 3280 | — | — | 2640 |
| Viscosity after 7 days (cps) | 3020 | 2475 | 2730 | 2810 |
| Viscosity after 8 days (cps) | 3000 | 1980 | 2140 | 2940 |
| Viscosity after 9 days (cps) | 2850 | 1990 | 2230 | 2870 |
| Appearance | clear | clear | clear | yellow |

*Hydroxypropylated waxy maize not thermally-inhibited.

EXAMPLE 25

This example shows the thermal inhibition of converted starches.

Samples of waxy maize and tapioca starch were slurried in 1.5 parts water. The slurries were placed in a 52° C. water bath, with agitation, and allowed to equilibrate for one hour. Concentrated hydrochloric acid was added at 0.8% on the weight of the samples. The samples were allowed to convert at 52° C. for one hour. The pH was then adjusted to 5.5 with sodium carbonate and then to pH 8.5 with sodium hydroxide. The samples were recovered by filtering and air drying (approximately 11% moisture). The starches in 50 g amounts were placed in an aluminum tray, covered and placed into a forced draft oven at 140° C. for 5.5 hours.

The starches were evaluated for inhibition. The results are shown below.

| Starches | Waxy Maize Viscosity (BU) | | | Tapioca Viscosity | | |
|---|---|---|---|---|---|---|
|  | Peak | Peak + 10' | Breakdown (%) | Peak | Peak + 10' | Breakdown (%) |
| Unmodified | 1380 | 250 | 81.9 | 810 | 225 | 72.2 |
| Acid-converted | 640 | 110 | 82.3 | 432 | 115 | 73.4 |
| T-I Acid-converted | 805 | 728 | 9.6 | 495 | 350 | 29.3 |

The results show that converted starches can be thermally inhibited by this process.

EXAMPLE 26

This example shows the preparation of potato starches modified with an amino-multicarboxylic acid (CEPA) reagent, i.e., 2-chloroethylaminodipropionic acid (hereinafter referred to as CEPA-starches) and their subsequent thermal-inhibition.

Deionized water (150 ml) was added to a liter beaker and heated to 45° C. with an external constant temperature bath. A total of 30 g sodium sulfate (30% on starch) was dissolved in the water followed by the addition of 100 g of the potato starch. A solution of 3% aqueous sodium hydroxide (25 ml) was added slowly with good agitation to minimize starch swelling. A 25% aqueous solution of the CEPA reagent (32 ml) to give an 8% starch treatment (dry basis) was added simultaneously with a 3% aqueous sodium hydroxide solution (170 ml). The addition rates used kept the level of caustic high so that pH was about 11.0 to 11.5 during the reaction. The reaction was run at 42°–45° C. for 16 hours and then neutralized by adding 3N hydrochloric acid to adjust pH to about 9.5, followed by stirring for 30 minutes. Overhead stirring was used throughout this reaction. The starch was then filtered and washed twice with 150 ml of water and allowed to air dry. Analysis of the starch for bound nitrogen showed 0.25% N (dry basis).

The pH 9.5 CEPA-starch was and heat treated at 100° C., 110° C., 120° C., 130° C. and 140° C. for 0 minutes using the fluidized bed previously described.

EXAMPLE 27

A granular waxy maize starch which had been lightly crosslinked with 0.04% phosphorous oxychloride was thermally-inhibited. The granular starch was jet-cooked and spray-dried using the coupled continuous jet-cooking/spray-drying process and conditions described in Example 9. The spray-dried starch was oven dehydrated and heat treated for 8 hours at 140° C.

The Brabender results and viscosity and textural characteristics of the resulting thermally-inhibited starch are set out below.

| Brabender Evaluation of Crosslinked and Jet-Cooked/Spray-Dried Waxy Maize - pH 8.7 | | | | | | |
|---|---|---|---|---|---|---|
|  | Viscosity (BU) | | | | | Break- |
|  | 30° C. | 30° C. + 10' | Peak | 95° C. | 95° C. + 10' | down (%) |
| Control | 150 | 165 | 215 | 120 | 70 | 67 |
| T-I Starch | 840 | 1,085 | 1,110 | 1,090 | 1,085 | 1 |

| Cook Evaluation of Crosslinked and Jet-Cooked/Spray-Dried/Waxy Maize - pH 8.7 | | |
|---|---|---|
|  | Viscosity of Cook | Texture of Cook |
| Control | thin to moderate | cohesive, pulpy |
| T-I Starch | very heavy | non-cohesive, very pulpy, short |

The results show that after the dehydration and heat treatment steps the crosslinked starch was very highly inhibited.

EXAMPLE 28

This example shows the use of thermally-inhibited, CEPA-modified potato starches in various aqueous-based skin lotions. The starches were dispersed in the aqueous phase.

The starches were prepared as in Example 26 using an aqueous solution of the CEPA reagent in an amount sufficient to provide 0.21% bound nitrogen (dry basis), adjusted to pH 9.5 before recovery of the CEPA starch, and thermally-inhibited at 110° C., 121° C., 129° C., and 140° C. for 0 minutes and 15 minutes, respectively using the fluidized bed previously described.

The thermally-inhibited, CEPA-modified potato starches were evaluated in three skin care formulations.

FORMULATION I

| INGREDIENTS | % |
|---|---|
| Phase A | |
| Cetyl Alcohol | 1.00 |
| Stearic Acid | 2.00 |
| Octyl Palmitate | 5.00 |
| $C_{12}$–$C_{15}$-Alkyl Benzoate | 5.00 |
| Dimethicone Copolyol | 1.00 |
| Phase B | |
| Deionized Water | 79.50 |
| Propylene Glycol | 3.00 |
| Triethanolamine (99%) | 0.50 |
| T-I, CEPA Potato Starch | 2.00 |
| Phase C | |
| Preservative | 1.00 |
| Total | 100.00 |

The ingredients of Phase B were combined, heated to 80° C., and held for 20 minutes. The ingredients of Phase A are combined and heated to 80° C. Phase A was added to Phase B at 80° C., mixed for 10 minutes, and cooled to 40° C. Phase C was added, and mixed thoroughly. The mixture was cooled to room temperature.

In the above formulation the starch's primary function is as a viscosifying agent and secondary function is an emulsion stabilizing agent. The stearic acid and triethanolamine act as the primary emulsifying system. Microscopic evaluations (150X) were performed to verify cooking of the starch. All samples except the starches thermally inhibited at 140° C. resulted in small particle size emulsions. The sample inhibited at 140° C. was grainy in texture.

FORMULATION II

| INGREDIENTS | % |
|---|---|
| Phase A | |
| Cetyl Alcohol | 1.00 |
| Octyl Palmitate | 5.00 |
| $C_{12}$–$C_{15}$-Alkyl Benzoate | 5.00 |
| Dimethicone Copolyol | 1.00 |
| Phase B | |
| Deionized Water | 82.00 |
| Propylene Glycol | 3.00 |
| T-I, CEPA Potato Starch | 2.00 |
| Phase C | |
| Preservative | 1.00 |
| Total | 100.00 |

The method described above for combining the ingredients and phases was used. In this formulation, the starch functions as a viscosifying agent and emulsifier/emulsion stabilizer. Cetyl alcohol also contributes to the emulsion stabilization.

FORMULATION III

| INGREDIENTS | % |
|---|---|
| Phase A | |
| Octyl Palmitate | 5.00 |
| $C_{12}$–$C_{15}$-Alkyl Benzoate | 5.00 |
| Dimethicone Copolyol | 1.00 |
| Phase B | |
| Deionized Water | 82.00 |
| Propylene Glycol | 3.00 |
| T-I, CEPA Potato Starch | 3.00 |
| Phase C | |
| Preservative | 1.00 |
| Total | 100.00 |

The above method for combining the ingredients and phases was used. In this formulation, the starch functions as a viscosifying agent and a primary emulsifier since no stearic acid, triethanolamine, or cetyl alcohol was used in the formulation.

Viscosity Stability

The viscosity of the above lotions was determined after 24 hours, and for some lotions, after 1 month. A Brookfield RV Helipath viscometer equipped with a T bar spindle and rotated at 10 rpm was used. The rheology and/or appearance was also determined.

The results are shown below.

FORMULATION I

| CEPA Potato Starch | Viscosity at 24 Hours (cps) | Viscosity at 1 Month (cps) | Rheology |
|---|---|---|---|
| Control (non-T-I CEPA-potato) | 7700 | Stable | short, slight snap |
| T-I at 110° C. for 0 min. | 16,068 | Stable | short, slight snap |
| T-I at 110° C. for 15 min. | 12,832 | Stable | short, slight snap |
| T-I at 121° C. for 0 min. | 15,932 | Stable | short, slight snap |
| T-I at 121° C. for 15 min. | 16,232 | Stable | short, slight snap |
| T-I at 129° C. for 0 min. | 16,000 | Stable | short, slight snap |
| T-I at 129° C. for 15 min. | 18,732 | Stable | short, little to no snap |
| T-I at 140° C. for 0 min. | 19,732 | Stable | did not cook out |
| T-I at 140° C. for 15 min. | 18,132 | Stable | did not cook out |

N.D. — not determined.

FORMULATION II

| CEPA Potato Starch | Viscosity at 24 Hours (cps) | Appearance |
|---|---|---|
| Control (non-T-I CEPA-potato) | 22,933 | gel-like |
| T-I at 110° C. for 0 min. | 31,932 | gel-like |

-continued

| T-I at 110° C. for 15 min. | 19,032 | gel-like |
| T-I at 121° C. for 0 min. | 31,132 | gel-like |
| T-I at 121° C. for 15 min. | 13,968 | lotion |
| T-I at 129° C. for 0 min. | 11,658 | lotion |
| T-I at 129° C. for 15 min. | 7268 | lotion |
| T-I at 140° C. for 0 min. | 4100 | did not cook out thoroughly |
| T-I at 140° C. for 15 min. | 3800 | did not cook out thoroughly |

FORMULATION III

| CEPA Potato Starch | Viscosity at 24 Hours (cps) | Appearance |
|---|---|---|
| Control (non-T-I CEPA potato) | 24,632 | gel |
| T-I at 110° C. for 0 min. | 14,932 | gel |
| T-I at 110° C. for 15 min. | 14,932 | gel |
| T-I at 121° C. for 0 min. | 17,132 | gel |
| T-I at 121° C. for 15 min. | 15,468 | gel |
| T-I at 129° C. for 0 min. | 18,600 | gel |
| T-I at 129° C. for 15 min. | 15,300 | gel |
| T-I at 140° C. for 0 min. | 14,232 | did not cook out thoroughly |
| T-I at 140° C. for 15 min. | 14,168 | did not cook out thoroughly |

The results show that the low temperature (110°–129° C.) thermal-inhibition of CEPA-modified potato starches significantly improved the viscosity and improved the textural and/or rheological properties. The CEPA-modified potato starches which were thermally inhibited at 110° and 121° C. for 0 and 15 minutes and at 129° C. for 0 minutes were very similar; their viscosities were significantly higher than the control and their rheology/appearance was shorter (slight snap) than the control. The thermally-inhibited starches both had a short texture and slight snap. The Control was slightly stringier. The CEPA-modified potato starch which was thermally inhibited at 129° C. for 15 minutes performed best in Formulation I giving a much higher viscosity and little to no snap.

EXAMPLE 29

This example describes the evaluation of highly inhibited derivatized granular waxy maize starches in various aqueous-based hair care products. The starches were dispersed by cooking in water and added as a 10% solution to the various hair care products.

Hydroxypropylated waxy maize starches, derivatized with 3% propylene oxide (PO), were adjusted to pH 9.5 and dehydrated and heat treated in the fluidized bed for 60, 90 and 120 minutes at 160° C. The viscosities reported are Brookfield viscosities measured using a Brookfield RV Helipath viscometer rotated at 10 rpm. Spindle A was used for the shampoo and hair dye; spindle B was used for the alkaline conditioners. An average of 10 readings was taken.

Part A—Shampoo Formulation

A shampoo was formulated by mixing the following ingredients.

| Ingredients | SLS Shampoo (%) |
|---|---|
| Sodium Lauryl Sulfate (SLS) (29%) | 58.62 |
| Sodium Lauryl Ether Sulfate (SLES) (60%) | |
| Lauric Diethanolamide | 3.00 |
| T-I - PO Starch (10%) | 25.00 |
| Citric Acid (10%) | 3.00 |
| Water | to 100% |

The base starch was adjusted to pH 9.5 and thermally-inhibited by heating for 120 minutes at 160° C. A blank containing water in place of the starch in the above shampoo system was used as the negative control.

The viscosity results are shown below:

| Shampoo Formulation | Viscosity (cps) |
|---|---|
| SLS Shampoo + Base Starch | 7226 |
| SLS Shampoo + T-I Starch | 11,640 |
| SLS Control | 1636 |

The results show that the thermally-inhibited starch is an effective thickener, with a significantly increased viscosity compared to the base starch. The T-I starch appeared to be more compatible in the SLS shampoo than the base starch.

Part B—Hair Dye Base Formulation

The formulation contained the following ingredients:

| Ingredients | % |
|---|---|
| p-Phenylene Diamine | 0.50 |
| Resorcinol | 0.50 |
| 1-Napthol | 0.01 |
| Sodium Sulfite | 0.10 |
| Hexylene Glycol | 2.00 |
| Carbitol | 4.00 |
| Ammonium Hydroxide (28%) | 5.77 |
| Ammonium Chloride | 2.84 |
| Sodium Lauryl Sulfate (30%) | 2.00 |
| Sodium Chloride | 0.20 |
| Starch (10%) | 50.00 |
| Water | to 100% |

The base starch was adjusted to pH 9.5 and thermally-inhibited by heating for 120 minutes at 160° C. A blank containing water in place of the starch in the above hair dye formulation was used as the negative control.

The viscosity results are shown below.

| Hair Dye | Viscosity (cps) |
|---|---|
| Waxy Maize (pH 9.5) | 1326 |
| T-I Waxy Maize (pH 9.5;120 min. at 160° C.) | 4740 |
| Control | 50 |

The results show that the thermally-inhibited starch is an effective thickener which significantly increased the viscosity.

Part C—Alkaline Conditioners

Conditioners A to D contained the following ingredients:

| Ingredient | A (%) | B (%) | C (%) | D (%) |
|---|---|---|---|---|
| Ammonium hydroxide (30%) | 6.67 | 6.67 | 6.67 | — |
| Cetrimonium chloride (25%) | — | 4.00 | — | — |
| Polyquaternium 6 (40%) | — | — | 2.50 | — |
| Starch (10%) | 50.00 | 50.00 | 50.00 | 50.00 |
| Water | to 100% | to 100% | to 100% | to 100% |

The base starch was adjusted to pH 9.5 and thermally-inhibited by heating for 60, 90, and 120 minutes at 160° C. A blank containing water and no starch was used as the negative control.

The viscosity results after storage at 25° C. for the indicated number of days are shown below.

| Waxy Maize | Conditioner | Viscosity (cps) | | | | |
|---|---|---|---|---|---|---|
| | | Day 1 | Day 7 | Day 14 | Day 22 | Day 28 |
| Base | A | 1100 | 1140 | 1100 | 960 | 892 |
| (pH 9.5) | B | 2300 | 2520 | 2172 | 1692 | 1440 |
| | C | 3460 | 3720 | 3312 | 3132 | 2952 |
| | D | 800 | 1220 | 700 | 132 | 0 |
| T-I | A | 7060 | 7152 | 6380 | 6072 | 5960 |
| (pH 9.5; | B | 2420 | 2780 | 2540 | 2400 | 2380 |
| 60 min. | C | 9472 | 11,660 | 9892 | 9352 | 8952 |
| at 160°) | D | 4860 | 5860 | 5400 | 5340 | 5440 |
| T-I | A | 5780 | 5992 | 5260 | 4872 | 4800 |
| (pH 9.5; | B | 2752 | 3080 | 2412 | 2420 | 2412 |
| 90 min. | C | 10,600 | 10,780 | 10,300 | 9352 | 9492 |
| at 160°) | D | 4472 | 5440 | 5092 | 4900 | 5652 |
| T-I | A | 6472 | 6892 | 5900 | 5680 | 5420 |
| (pH 9.5; | B | 3092 | 2540 | 2712 | 2408 | 2312 |
| 120 min. | C | 12,832 | 12,732 | 12,880 | 11,792 | 11,680 |
| at 160°) | D | 6332 | 7120 | 6440 | 5652 | 6412 |
| Blank | A | 0 | 0 | 0 | 0 | 0 |
| | B | 0 | 0 | 0 | 0 | 0 |
| | C | 0 | 0 | 0 | 0 | 0 |
| | D | 0 | 0 | 0 | 0 | 0 |

The results show that in Systems A, C, and D all the thermally-inhibited starches were satisfactory thickeners and were better than the base starch. Viscosity stability was very good at room temperature for most of the systems. Viscosity decreases were seen at an elevated temperature (45° C.) in Systems A, B, and C. The base starch showed significant viscosity loss at elevated temperatures in all systems. Performance was only comparable to the base starch in System B, the system containing the monomeric thickener cetrimonium chloride; the long term stability of System B at elevated temperatures was also poor with phase separation occurring. The polymeric thickener polyquaternium 6 (System C) appears to thicken synergistically with all the thermally-inhibited starches; however, over time System C also exhibited some incompatibility with the thermally-inhibited starches at elevated temperature, with a darker yellow color at the bottom but with no distinct phase separation. The base starch did not exhibit this high temperature incompatibility.

EXAMPLE 30

This example shows the use of thermally-inhibited granular corn starch derivatized with 2% octenylsuccinic acid (OSA) and crosslinked with 2% aluminum sulfate (referred to as A1-OSA starches) in an aqueous-based lotion as an asethetic-modifying agent. Modification with the ocentylsuccinic anhydride (OSA) renders the starch hydrophobic. The derivatized crosslinked starch was adjusted to pH 9.5 and heat treated for the indicated time.

The ingredients are shown below:

| | No. 1 | No. 2 |
|---|---|---|
| Phase A | | |
| Cetyl Alcohol | 1.00 | 1.00 |
| Cetech 20 | 1.00 | 1.00 |
| Glyceryl Stearate | 1.00 | 1.00 |
| $C_{12}$–$C_{15}$ Alkyl benzoate | 5.00 | 5.00 |
| Octyl Palmitate | 5.00 | 5.00 |
| Stearic Acid | 2.00 | 2.00 |
| Dimethicone Copolyol | 1.00 | 1.00 |
| Phase B | | |
| Deionized Water | 65.30 | 65.30 |
| Carbopol 941 (2% aqueous solution) | 10.00 | 10.00 |
| Triethanolamine (99%) | 0.70 | 0.70 |
| Propylene glycol | 3.00 | 3.00 |
| T-I Al—OSA corn (pH 9.5; 160° C. for 30 min) | 4.00 | — |
| T-I Al—OSA corn (pH 9.5; 160° C. for 90 min) | — | 4.00 |
| Phase C | | |
| Preservative | 1.00 | 1.00 |
| | 100.00 | 100.00 |

The ingredients of Phase B were combined, except for the propylene glycol and the starch, and heated to 80° C. The ingredients of Phase A were combined, heated to 80° C. and added to Phase B at 80° C. and mixed for 10 minutes. The starch was slurried in the propylene glycol and added at 70° C. to combined Phases A and B. The mixture was cooled to 40° C. and Phase C was added, mixed thoroughly, and cooled to room temperature.

The viscosity profile of the lotion is shown below. The control is the non-thermally-inhibited crosslinked derivatized starch. The Helipath Brookfield viscosity was measured at 10 rpm using a TC spindle.

The results are shown below.

| Starch | Initial Viscosity (cps) |
|---|---|
| Control | 48,500 |
| T-I (160° C. for 30 min.) | 21,900 |
| T-I (160° C. for 90 min.) | 32,500 |

Microscopic evaluation showed that the thermally-inhibited starches maintained their birefringence. The lotions were stable after one month. They exhibited increased temperature stability over the control. The thermal inhibition improves heat stability of the starches and hence the starches can be added to higher temperature emulsions than can be done with non-thermally-inhibited crosslinked starches.

EXAMPLE 31

This example describes the use of a thermally-inhibited granular starch in a shaving cream.

| Ingredients | % |
|---|---|
| Phase A | |
| Stearic Acid T.P. | 8.00 |
| Phase B | |
| Deionized Water | 76.80 |
| Sodium Lauryl Sulfate (28–30%) | 7.00 |
| Triethanolamine 99% | 0.70 |
| T-I CEPA Potato Starch (130° C. for 0 min) | 2.00 |
| Phase C | |
| Propylene glycol (and) Diazolidinyl Urea (and) Methylparaben (and) Propylparaben (Preservative) | 1.00 |
| Phase D | |
| Fragrance | 0.20 |
| Total | 100.00 |

The ingredients of Phase B are combined with agitation and heated to 80° C. In a separate vessel the ingredients of Phase A are heated to 80° C. At 80° C. Phase A is added to Phase B, mixed for 15 minutes, and cooled to 40° C. Phases C and D are added to Phases A and B, mixed thoroughly, and cooled to room temperature.

The concentrate is packaged in aerosol cans using 96.5% concentrate and 3.5% isobutane propellant.

EXAMPLE 32

This example describes the preparation of an aqueous-based, water-resistant sunscreen containing a thermally-inhibited granular starch.

| Ingredients | % |
|---|---|
| Phase A | |
| Octyl Methoxycinnimate | 5.00 |
| Benzophenone-3 | 2.00 |
| $C_{12}$–$C_{15}$ Alkyl Benzoate | 7.00 |
| Isopropyl Palmitate | 4.00 |
| Lanolin Oil | 0.50 |
| DEA Cetyl Phosphate | 1.00 |
| Phase B | |
| Deionized Water | 74.50 |
| Butylene Glycol | 3.00 |
| T-I CEPA Potato (130° C. for 0 min) | 2.00 |
| Phase C | |
| Propylene Glycol (and) Diazolidinyl Urea (and) Methylparaben (and) Propylparaben | 1.00 |
| Total | 100.00 |

The thermally-inhibited starch is sifted into the deionized water and butylene glycol. The mixture is heated to 80° C. and held for 20 minutes. The ingredients of Phase A are combined and heated to 80° C. Phase A is added to Phase B at 80° C., mixed for 10 minutes, and cooled to 40° C. Phase C is added, mixed thoroughly, cooled to room temperature, and the resulting mixture is packaged.

EXAMPLE 33

The example describes the preparation of an aqueous-based lotion containing an alpha-hydroxy acid and a thermally-inhibited granular modified starch as a thickening agent.

| Ingredients | % |
|---|---|
| Phase A | |
| Isopropyl Palmitate | 6.50 |
| Stearic Acid T.P. | 4.00 |
| PEG 100 Stearate | 2.00 |
| Glyceryl Stearate | 2.00 |
| Cetyl Alcohol | 1.50 |
| Isostearic Acid | 1.00 |
| Dimethicome 100 cst | 1.00 |
| PEG 40 Stearate | 0.50 |
| Phase B | |
| Deionized Water | 59.65 |
| Ammonium Hydroxide 28% | 4.00 |
| Butylene Glycol | 7.00 |
| Sorbitan Stearate | 0.50 |
| T-I Potato Starch (pH 9.5; 125° C. for 0 min) | 2.00 |
| Phase C | |
| Glycolic Acid (70%) | 8.00 |
| Phase D | |
| Imidazolidinyl Urea | 0.35 |
| Total | 100.00 |

The ingredients of Phase B are combined, heated to 80° C., and mixed for 20 minutes. The ingredients of Phase A are combined and heated to 80° C. Phase A is added to Phase B at 80° C., mixed for 10 minutes, and cooled to 60° C. Phase C is added, mixed thoroughly, and cooled to 40° C. Phase D is added, and the mixture is packaged.

EXAMPLE 34

This example describes the preparation of an aqueous-based cream containing an alpha-hydroxy acid and a CEPA-modified thermally-inhibited granular potato starch as a thickener/emulsion stabilizer.

| Ingredients | % |
|---|---|
| Phase A | |
| Caprylic/Capric Triglyceride | 8.00 |
| Stearic Acid T.P. | 4.00 |
| Isopropyl Palmitate | 5.00 |
| Glyceryl Stearate | 2.00 |
| PEG-100 Stearate | 1.00 |
| Cetyl Alcohol | 1.00 |
| Isostearic Acid | 1.00 |
| Palmitamidopropyl Dimethylamine | 1.00 |
| Phase B | |
| Deionized Water | 58.20 |
| Propylene Glycol | 8.00 |
| Methylparaben | 0.15 |
| Propylparaben | 0.10 |
| T-I CEPA Potato (130° C. for 0 min) | 2.00 |
| Phase C | |
| Polyacrylamide/$C_{13-14}$ isoparaffin/Laureth-7 | 1.00 |
| Phase D | |
| Glycolic Acid (70%) | 7.20 |
| Phase E | |
| Imidazolidinyl Urea | 0.35 |
| Total | 100.00 |

The ingredients of Phase B are combined with agitation, heated to 80° C., and held for 20 minutes. The ingredients of Phase A are combined and heated to 80° C. Phase A is added to Phase B at 80° C., mixed for 10 minutes, and cooled to 75° C. Phase C is added, mixed thoroughly, and cooled to 60° C. Phase D is added, mixed thoroughly, and cooled to 40° C. Phase E is added, mixed thoroughly, and cooled to room temperature.

EXAMPLE 35

This example describes the preparation of an aqueous-based daily UV protection liquid makeup containing a thermally-inhibited granular unmodified potato starch as a thickener.

| Ingredients | % |
|---|---|
| Phase A | |
| Octyl Methoxycinnamate | 3.00 |
| Benzophenone 3 | 2.00 |
| Isopropyl Palmitate | 6.00 |
| Phenyl Trimethicone | 2.00 |
| Stearic Acid T.P. | 2.00 |
| Propylene Glycol Dicaprylate/Caprate | 8.00 |
| Sunflower Oil | 3.00 |
| Cetyl Alcohol | 1.00 |
| Phase B | |
| Deionized Water | 52.15 |
| Butylated Hydroxyanisole | 0.10 |
| Trisodium EDTA | 0.05 |
| DEA Cetyl Phosphate | 1.00 |
| Methylparaben | 0.15 |
| Propylparaben | 0.10 |
| T-I Potato Starch (pH 9.5; 125° C. for 0 min) | 2.00 |
| Phase C | |
| Titanium Dioxide | 4.50 |
| Red Iron Oxide | 0.50 |
| Yellow Iron Oxide | 3.00 |
| Black Iron Oxide | 0.10 |
| Phase D | |
| Propylene Glycol | 3.00 |
| Aluminum Starch Octenyl Succinate | 3.00 |
| Tocopheryl Acetate | 1.00 |
| Phase E | |
| Diazolidinyl Urea | 0.15 |
| Total | 100.00 |

The ingredients of Phase C are blended until uniform. The thermally-inhibited starch is dispersed in the ingredients of Phase B and heated to 80° C. and held for 20 minutes. The ingredients of Phase C are slowly sifted in and mixed thoroughly into Phase B. The ingredients of Phase A are combined, heated to 80° C., added to the combination of Phase B and C at 80° C., mixed for 15 minutes, and cooled to 40° C. Phase D is slurried, added at 40° C., and mixed thoroughly. Phase E is added and mixed in. The mixture is cooled to room temperature and packaged.

EXAMPLE 36

This example describes the use of a thermally-inhibited granular crosslinked hydrophobic cornstarch in a dry matte lipstick as an aesthetic modifier.

| Ingredients | % |
|---|---|
| Phase A | |
| Octyl Dodecanal | 14.00 |
| Acrylates/Octylacrylamide Copolymer | 1.00 |
| Phase B | |
| Cyclomethicone (and) Quaternium-18 Hectorite (and) Propylene Carbonate | 23.00 |
| Cyclomethicone | 9.95 |
| Caprylic/Capric Triglycerides | 5.00 |
| Octyl Dodecyl Stearate | 0.50 |
| Triglycerol Disostearate | 4.00 |
| Tocopheryl Acetate | 0.10 |
| Silica Silylate | 0.50 |
| T-I Aluminum Corn Starch Octenyl Succinate (pH 9.5; 160° C. for 30 min.) | 20.00 |
| Iron Oxide | 0.50 |
| Carmine Red | 0.50 |
| Ultramarine Blue | 0.50 |
| D&C Red #6 (30% dispersion in Castor Oil) | 5.00 |
| Titanium Dioxide (30% dispersion in Castor Oil) | 1.75 |
| Bismuth oxychloride | 1.00 |
| Phase C | |
| Microcrystalline Wax | 2.00 |
| Carnauba Wax | 4.00 |
| Ozokerite Wax | 2.00 |
| Candelilla Wax | 4.50 |
| Total | 100.00 |

The ingredients of Phase A are combined with agitation and heated to 80° C. The ingredients of Phase B are combined and mixed until the colors are uniform. Phase B is added to Phase A at 80° C. and mixed thoroughly. Phase C is added, mixed in until the mixture is uniform, and cooled to 65° C. Phase D is added and mixed well. The mixture is poured into molds and cooled to room temperature.

EXAMPLE 37

This example describes the preparation of a velvety dusting powder.

| Ingredients | % |
|---|---|
| Phase A | |
| Talc | 77.40 |
| T-I Aluminum Corn Starch Octenyl Succinate (pH 9.5; 160° C. for 30 min) | 20.00 |
| Zinc stearate | 2.00 |
| Methylparaben | 0.10 |
| Propylparaben | 0.10 |
| Diazolidinyl Urea (Germall II available from Sutton Labs.) | 0.20 |
| Phase B | |
| Fragrance | 0.20 |
| Total | 100.00 |

The ingredients of Phase A are mixed for 10–15 minutes using a P-K liquid solid blender. The fragrance of Phase B is sprayed into Phase A and mixed thoroughly. The thermally-inhibited starch should impart a smooth silky skin feel and natural look and resist caking and agglomeration.

EXAMPLE 38

This example describes the preparation of a pressed powder.

| Ingredients | % |
|---|---|
| Phase A | |
| Zinc Stearate | 3.00 |
| T-I Aluminum Corn Starch Octenylsuccinate (pH 9.5; 160° C. for 90 min) | 25.00 |
| Imidazolidinyl Urea | 0.20 |
| Talc | 39.80 |
| Red Iron Oxide 7051 (50% in Talc 5251) | 14.00 |
| Brown Iron Oxide 7061 (50% in Talc 5251) | 2.00 |
| Black Iron Oxide 7133 (50% in Talc 5251) | 0.30 |
| D&C Red #6 (25% in Talc 141) | 2.25 |
| Color Blend | 6.45 |
| Phase B | |
| Isopropyl Myristate | 3.00 |
| Caprylic/Capric Triglyceride | 2.00 |
| Isoeicosane | 2.00 |
| Total | 100.00 |

The ingredients of Phase A are blended until uniform. The ingredients of Phase B are added to Phase A, and the mixture is blended until uniform and pressed at 1500 psi.

EXAMPLE 39

This example describes the preparation of topical spray powder.

| Ingredients | % |
|---|---|
| Anhydrous Ethanol, SDA-40 | 42.00 |
| Aminomethyl Propanol 95% | 0.38 |
| Acrylates/Octylacrylamide Copolymer | 2.00 |
| T-I Aluminum Corn Starch Octenylsuccinate (pH 9.5; 160° C. for 30 min) | 10.00 |
| Isobutane Propellant | 45.62 |
| | 100.00 |

The aminomethyl propanol is dissolved in ethanol. While maintaining good agitation, the copolymer is slowly sifted in. When solution is complete, the thermally-inhibited starch is sifted in and mixed well until the mixture is homogeneous. The cans are then filled.

EXAMPLE 40

This example shows the preparation of a daily UV protection lotion (approximate SPF 18).

| Ingredients | % |
|---|---|
| Phase A | |
| Octyl Methoxycinnamate | 7.50 |
| Steareth 10 | 1.00 |
| Glyceryl Stearate SE | 1.50 |
| Stearic Acid T.P. | 1.50 |
| Titanium Dioxide/$C_{12-15}$ Alkyl Benzoate | 1.70 |
| $C_{12-15}$ Alkyl Benzoate | 5.00 |
| Cyclomethicone | 3.00 |
| Phenyl Trimethicone | 1.00 |
| Dimethicone Copolyol | 0.50 |
| Phase B | |
| Deionized Water | 40.30 |

| Ingredients | % |
|---|---|
| Triethanolamine (99%) | 4.00 |
| Acrylates/Octylacrylamide Copolymer | 1.00 |
| 2-Phenylbenzimidazole-5-Sulfonic Acid | 4.00 |
| Carbomer 940 (2% Aq. Soln) | 20.00 |
| Phase C | |
| Propylene Glycol | 3.00 |
| T-I Aluminum Corn Starch Octenylsuccinate (pH 9.5; 160° C. for 30 min) | 3.00 |
| Phase D | |
| Propylene Glycol (and) Diazolidinyl Urea (and) Methylparaben (and) Propylparaben | 1.00 |
| | 100.00 |

The triethanolamine and deionized water are combined and heated to 60° C. The copolymer is slowly sifted in and the mixtures is heated to 80° C. When the mixing is completed, the other ingredients are sifted in and mixed. The ingredients of Phase A are combined, heated to 80° C., added to the combined Phase B at 80° C. and mixed for 15–30 minutes. After cooling to 40° C., the thermally-inhibited starch is slurried in propylene glycol, added to Phases A and B at 40° C. and mixed thoroughly. Phase D is added. The mixture is cooled to room temperature and packaged.

EXAMPLE 41

This example describes the preparation of a mineral oil-free moisturizing hand and body lotion.

| Ingredients | % |
|---|---|
| Phase A | |
| N-Butyl Stearate | 8.00 |
| Cetyl Octanoate | 5.00 |
| Isopropyl Palmitate | 5.00 |
| Stearic Acid T.P. | 3.00 |
| Cetyl Alcohol | 1.00 |
| Lanolin Alcohol | 0.50 |
| Glyceryl Stearate SE | 2.00 |
| PEG 100 Stearate | 1.50 |
| Dimethicone Copolyol | 1.00 |
| Cyclomethicone | 3.00 |
| Phenyl Trimethicone | 1.00 |
| Tocopheryl Acetate | 1.00 |
| Phase B | |
| Deionized Water | 50.30 |
| Triethanolamine (99%) | 1.25 |
| Carbomer 941 (2% aq. soln.) | 10.00 |
| Methylparaben | 0.15 |
| Propylparaben | 0.10 |
| Trisodium EDTA | 0.05 |
| Acrylates/Octylacrylamide Copolymer | 1.00 |
| Phase C | |
| Propylene Glycol | 3.00 |
| T-I Aluminum Corn Starch Octenylsuccinate (pH 9.5; 160° C./90 min) | 2.00 |
| Phase D | |
| Diazolidinyl Urea | 0.15 |
| Total | 100.00 |

The ingredients of Phase B, except the copolymer, are combined and heated to 80° C. The copolymer is slowly sifted in and mixed until complete. The ingredients of Phase A are combined and heated to 80° C. Phase A is added to Phase B at 80° C., mixed for 15 minutes, and cooled to 40° C. The thermally-inhibited starch is slurried into propylene glycol, and Phase C is added at 40° C. and mixed thoroughly. Phase D is added and mixed until uniform. The mixture is cooled to room temperature and packaged.

EXAMPLE 42

This example describes a liquid make-up.

| Ingredients | % |
|---|---|
| Phase A | |
| N-Butyl Stearate | 10.00 |
| Cetyl Palmitate | 5.00 |
| Glyceryl Stearate SE | 2.00 |
| Methyl Glucose Sesquistearate | 1.50 |
| Stearic Acid T.P. | 2.00 |
| Phenyl Trimethicone | 2.00 |
| Phase B | |
| Deionized Water | 58.30 |
| Magnesium Aluminum Silicate | 0.75 |
| Cellulose Gum | 0.15 |
| Triethanolamine (99%) | 0.75 |
| Acrylates/Octylacrylamide Copolymer | 1.00 |
| DEA Cetyl Phosphate | 1.00 |
| $Na_3$ EDTA | 0.05 |
| Methylparaben | 0.15 |
| Propylparaben | 0.10 |
| Phase C | |
| 328 Titanium Dioxide | 4.50 |
| Red Iron Oxide | 0.50 |
| Yellow Iron Oxide | 3.00 |
| Black Iron Oxide | 0.10 |
| Phase D | |
| Butylene Glycol | 3.00 |
| T-I Aluminum Corn Starch Octenylsuccinate | 3.00 |
| (pH 9.5; 160° C. for 30 min.) | |
| Tocopheryl Acetate | 1.00 |
| Phase E | |
| Diazolidinyl Urea | 0.15 |
| Total | 100.00 |

Phase C is blended until uniform. For Phase B, the magnesium aluminum silicate and cellulose gum are dispersed into the deionized water and heated to 60° C. The remaining ingredients, except the copolymer, are added and mixed thoroughly. The copolymer is slowly sifted in, heated to 80° C., and mixed thoroughly. Phase C is slowly sifted into Phase B at 80° C. and mixed thoroughly. The ingredients of Phase A are combined, heated to 80° C., and Phase A is added to combined Phases B and C at 80° C. over 15 minutes. The mixture is cooled to 40° C. Phase D is slurried, added at 40° C., and mixed thoroughly. Phase E is added and mixed until complete. The mixture is cooled to room temperature and packaged.

EXAMPLE 43

This example describes an antiperspirant stick.

| Ingredients | % |
|---|---|
| Cyclomethicone | 47.00 |
| Glycol Distearate | 1.00 |
| Glyceryl Stearate and PEG 100 Stearate | 1.00 |
| PPG-3 Myristyl Ether | 5.00 |

| Ingredients | % |
|---|---|
| Stearyl Alcohol | 20.00 |
| Aluminum Zirconium Tetrachlorohydrex-Glycine | 20.00 |
| T-I Aluminum Corn Starch Octenyl Succinate | 6.00 |
| (pH 9.5; 160° C. for 90 min) | |
| Total | 100.00 |

The first four ingredients are combined and heated to 65° C. The stearyl alcohol is added and thoroughly mixed in. The aluminum zirconium tetrachorohydrex-glycine is added and mixed for 10 minutes. The thermally-inhibited starch is added and thoroughly mixed in. The mixture is cooled to 50° C., poured into molds, and cooled to room temperature.

EXAMPLE 44

This example describes the preparation of an after shave balm.

| Ingredients | % |
|---|---|
| Phase A | |
| N-butyl Stearate | 4.00 |
| Cetyl Palmitate | 2.50 |
| Myristyl Propionate | 3.00 |
| Mineral Oil and PEG-30 Lanolin and Cetyl Alcohol | 1.50 |
| Phase B | |
| Deionized Water | 61.60 |
| Lecithin | 1.00 |
| Carbomer (2% Aq. Soln.) | 10.00 |
| NaOH (25%) | 0.40 |
| Methylparaben | 0.15 |
| Propylparaben | 0.15 |
| Phase C | |
| Glycerin (99.5%) | 7.00 |
| T-I Aluminum Corn Starch Octenylsuccinate | 8.00 |
| (pH 9.5; 160° C. for 30 min) | |
| Phenoxyethanol | 0.20 |
| Phase D | |
| Fragrance | 0.50 |
| Total | 100.00 |

The ingredients of Phase B and Phase A are separately combined and heated to 80° C. Phases A and B are then combined, mixed for 15 minutes, and cooled to 40° C. The thermally-inhibited starch is slurried into the glycerin and added to combined Phases A and B at 40° C. The phenoxyethanol is added and mixed well. Phase D is added and mixing is continued until the mixture is uniform.

EXAMPLE 45

This example describes the preparation of a cream-to-powder eye shadow.

| Ingredients | % |
|---|---|
| Phase A | |
| Octyl Dodecanol | 13.00 |
| Acrylates/Octylacrylamide Copolymer | 1.00 |

-continued

| Ingredients | % |
| --- | --- |
| Phase B | |
| Microcrystalline Wax | 0.30 |
| Cyclomethicone (and) Quaternium-18 Hectorite (and) Propylene Carbonate | 30.00 |
| Phase C | |
| Caprylic/Capric Triglycerides | 3.00 |
| Octyl Dodecyl Stearate | 0.50 |
| Triglycerol Diisostearate | 4.00 |
| Tocopheryl Acetate | 0.10 |
| $C_{11-12}$ Isoparaffin | 7.40 |
| Silica Silylate | 0.50 |
| Mica (and) Iron Oxide (and) Titanium Dioxide | 10.00 |
| T-I Aluminum Corn Starch Octenylsuccinate (pH 9.5; 160° C. for 90 min) | 30.00 |
| Phenoxyethanol | 0.20 |
| Total | 100.00 |

The octyl dodecanol is heated to 80° C. The copolymer is added and mixed in until complete. The ingredients of Phase B are added and thoroughly mixed in. The ingredients of Phase C are combined and added to combined Phases A and B and mixed thoroughly. The mixture is cooled to room temperature.

EXAMPLE 46

This example describes the preparation of a roll-on antiperspirant.

| Ingredients | % |
| --- | --- |
| Cyclomethicone | 45.5 |
| Dioctyl Adipate | 10.0 |
| Quaternium 18-Hectorite, Propylene Carbonate | 14.0 |
| T-I Aluminum Corn Starch Octenyl Succinate (pH 9.5; 160° C. for 90 min) | 10.0 |
| Aluminum Zirconium Tetracholorohydrex-Gly | 20.0 |
| Silica | 0.50 |
| Total | 100.00 |

The cyclomethicone and quaternium 18-hectorite, propylene carbonate are mixed for 5 minutes. The thermally-inhibited starch is slurried into the dioctyl adipate. The slurry is added to the cyclomethicone mixture and mixed for 20 minutes. The aluminum zirconium tetracholohydrex-Gly is added and mixing is continued for 15 minutes. Silica is added and mixing is continued for 10 minutes. The suspension is packaged into roll-on applicators.

Now that the preferred embodiments of the present invention have been described in detail, various modifications and improvements thereto will become readily apparent to those skilled in the art. Accordingly, the spirit and scope of the invention are to be limited only by the appended claims and foregoing specification.

What is claimed:

1. A cosmetic composition selected from the group consisting of skin care compositions and hair care compositions which comprises a cosmetic vehicle and a thermally-inhibited starch or flour, wherein the thermally-inhibited starch or flour is a highly inhibited starch or flour present in an amount of about 0.3–90% by weight or a lightly inhibited starch or flour present in an amount of about 0.1–20% by weight, based on the weight of the cosmetic composition, and wherein the thermally-inhibited starch or flour is prepared by a process which consists essentially of the steps of (a) dehydrating an ungelatinized granular starch, a pregelatinized granular starch, a pregelatinized non-granular starch, or a flour to substantially anhydrous or anhydrous and (b) heat treating the substantially anhydrous or anhydrous starch or flour for up to 20 hours at 120° to 180° C., which time and temperature are sufficient to inhibit the starch or flour.

2. The composition of claim 1, wherein the thermally-inhibited starch or flour is a non-pregelatinized thermally-inhibited granular starch or flour which has an unchanged or reduced gelatinization temperature.

3. The composition of claim 1, wherein the thermally-inhibited starch flour is a pregelatinized granular or non-granular thermally-inhibited starch or flour.

4. The composition of claim 1, wherein an aqueous dispersion of the thermally-inhibited starch or flour is improved in viscosity stability in comparison to an aqueous dispersion of a non-thermally-inhibited flour of the same starch base.

5. The composition of claim 4, wherein the pH of the starch or flour is raised to neutral or greater prior to the dehydrating step.

6. The composition of claim 1, wherein the starch is a cereal starch, a tuber starch, a root starch, a legume starch, or a fruit starch and wherein the flour is a cereal flour, a tuber flour, a root flour, a legume flour, or a fruit flour.

7. The composition of claim 6, wherein the thermally-inhibited starch or flour is selected from the group consisting of corn, pea, oat, potato, sweet potato, banana, barley, wheat, rice, sago, amaranth, tapioca, sorghum, waxy maize, waxy tapioca, waxy rice, waxy barley, waxy potato, waxy sorghum, or a starch having an amylose content of 40% or greater.

8. The composition of claim 7, wherein the thermally-inhibited starch is corn, potato, rice, oat, waxy maize, waxy tapioca, waxy rice, waxy barley, or waxy potato and wherein the thermally-inhibited flour is tapioca flour.

9. The composition of claim 1, wherein the highly inhibited starch is about 0.5 to 30% and the lightly inhibited starch is about 0.3 to 8%.

10. The composition of claim 1, wherein the cosmetic vehicle is a liquid, an aerosol, or a semi-solid.

11. The composition of claim 10, wherein the liquid is an aqueous solution or aqueous emulsion, optionally containing an organic solvent, and wherein the thermally-inhibited starch or flour is dispersed in the aqueous solution in the effective thickening amount or in the aqueous phase of the emulsion in the effective emulsifying amount.

12. The composition of claim 11, wherein the emulsion contains about 10 to 90% by weight of an oil phase and about 90 to 10% by weight of a water phase containing the dispersed thermally-inhibited starch or flour.

13. The composition of claim 11, wherein the liquid is an organic solvent and wherein the thermally-inhibited starch is a granular thermally-inhibited starch which is present in non-dispersed form.

14. The composition of claim 11, wherein the vehicle is a semi-solid or an aerosol and wherein the thermally-inhibited starch is present dispersed in an aqueous liquid or in granular form.

15. The composition of claim 1, wherein the skin care composition is selected from the group consisting of a shaving cream, a lotion, a mousse, a cream, a sunscreen, a liquid makeup, a lipstick, a dusting powder, a pressed powder, a topical spray powder, an antiperspirant, an aftershave balm, and a cream-to-powder eye shadow mascara.

16. The composition of claim 1, wherein the starch is a thermally-inhibited granular starch; a thermally-inhibited pregelatinized granular starch; a thermally-inhibited pregelatinized non-granular starch; a thermally-inhibited granular starch derivatized with a non-ionic reagent or a hydrophobic reagent; or a thermally-inhibited granular starch derivatized with an amino-multicarboxylic acid reagent.

17. The composition of claim 16, wherein the starch is derivatized with the hydrophobic reagent ocentylsuccinic acid and optionally crosslinked with aluminum sulfate; wherein the starch is derivatized with the amino-multicarboxylic acid reagent α-chlorethylamino-dipropionic acid; or wherein the starch is derivated with the non-ionic reagent propylene oxide.

18. The composition of claim 1, wherein the hair care composition is selected from the group consisting of hair treatment compositions, hair styling aids, shampoos, and conditioners.

19. The composition of claim 18, wherein the hair care composition is an aqueous-based hair care composition and the thermally-inhibited starch is dispersed in the aqueous composition and wherein the hair treatment composition is selected from the group consisting of dyes, color rinses, bleaches, relaxers, and perms; and wherein the hair styling aids are selected from the group consisting of mousses, gels, pomades, and hair sprays.

\* \* \* \* \*